(12) United States Patent
Ogawa

(10) Patent No.: US 10,278,655 B2
(45) Date of Patent: May 7, 2019

(54) PHOTOGRAPHING DEVICE

(71) Applicant: Toshiba Medical Systems Corporation, Otawara-shi (JP)

(72) Inventor: Takayuki Ogawa, Bunkyo (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 572 days.

(21) Appl. No.: 15/054,354

(22) Filed: Feb. 26, 2016

(65) Prior Publication Data

US 2016/0270743 A1     Sep. 22, 2016

(30) Foreign Application Priority Data

Mar. 17, 2015  (JP) ................................. 2015-053750
Feb. 18, 2016  (JP) ................................. 2016-029280

(51) Int. Cl.
*A61B 6/00*     (2006.01)
*A61B 6/03*     (2006.01)

(52) U.S. Cl.
CPC ............ *A61B 6/035* (2013.01); *A61B 6/4233* (2013.01); *A61B 6/4411* (2013.01)

(58) Field of Classification Search
CPC ..... A61B 6/035; A61B 6/4233; A61B 6/4411; A61B 2017/00716; A61B 2034/105; A61B 6/032; A61B 6/504; H01L 2924/00014; H01L 2924/00; H01L 2224/48091; H01L 2924/181; H01L 2224/97; H01L 2924/12042; H01L 2924/30107;

(Continued)

(56) References Cited

U.S. PATENT DOCUMENTS 6,396,898 B1 *  5/2002  Saito ..................... G01N 23/046
                                                          378/19
6,990,176 B2 *  1/2006  Sherman ................ A61B 6/032
                                                          250/370.09

(Continued)

FOREIGN PATENT DOCUMENTS

EP      0 109 206 A2    5/1984
JP      60-90539        5/1985
JP      2007-512075     5/2007

*Primary Examiner* — Irakli Kiknadze
(74) *Attorney, Agent, or Firm* — Oblon, McClelland, Maier & Neustadt, L.L.P.

(57) ABSTRACT

According to one embodiment, a photographing device includes a plurality of detectors and a plurality of supporting members. The detectors detect electromagnetic waves. The supporting members support the detectors and are cylindrically arranged adjacent to each other. Each supporting member includes a first protrusion and two second protrusions. The first protrusion is provided on one side face of each supporting member in the circumferential direction of the cylindrical arrangement of the supporting members, and protrudes in the circumferential direction. The two second protrusions protrude in the circumferential direction from the other side face of each supporting member, are provided with a gap greater than the width of the first protrusion in an intersecting direction that intersects with the circumferential direction of the cylindrical arrangement, and overlap with the first protrusion of a neighboring supporting member in the intersecting direction.

13 Claims, 17 Drawing Sheets

(58) Field of Classification Search
CPC ..... H01L 2924/351; H01L 2924/00012; H01L 2924/13055; H01L 2924/13091; H01L 2224/45015; H01L 2224/45099; H01L 2224/45144; H01L 2924/3011; H01L 2924/0002; H01L 2924/19107; H01L 23/53295; G02B 6/42; G02B 6/421; G02B 6/4219; G02B 6/4224; G01N 21/05; G01N 21/41; G01N 21/47
USPC .......................................... 378/4, 5, 19, 98.8
See application file for complete search history.

(56) References Cited

U.S. PATENT DOCUMENTS

| | | | | |
|---|---|---|---|---|
| 7,029,302 B2* | 4/2006 | Sawaya | ................. | A61B 6/032 439/260 |
| 7,117,588 B2* | 10/2006 | Vafi | ................. | H01L 27/14658 29/829 |
| 7,465,931 B2* | 12/2008 | Vogtmeier | ........... | A61B 6/4233 250/370.09 |
| 7,606,346 B2* | 10/2009 | Tkaczyk | ................ | A61B 6/032 250/370.09 |

* cited by examiner

US 10,278,655 B2

PHOTOGRAPHING DEVICE

CROSS-REFERENCE TO RELATED APPLICATIONS

This application is based upon and claims the benefit of priority from Japanese Patent Applications No. 2015-053750, filed on Mar. 17, 2015 and No. 2016-29280, filed on Feb. 18, 2016; the entire contents of which are incorporated herein by reference.

FIELD

Embodiments described herein relate generally to a photographing device.

BACKGROUND

A photographing device such as an X-ray computed tomography device is known, which includes a plurality of supporting members in a curved shape to support a plurality of detectors of electromagnetic waves such as X-rays.

It is useful to facilitate a replacing work for any one of the supporting members.

In view of this, it is an objective of an embodiment to provide a photographing device including easily replaceable supporting members.

DETAILED DESCRIPTION

Figure 1:
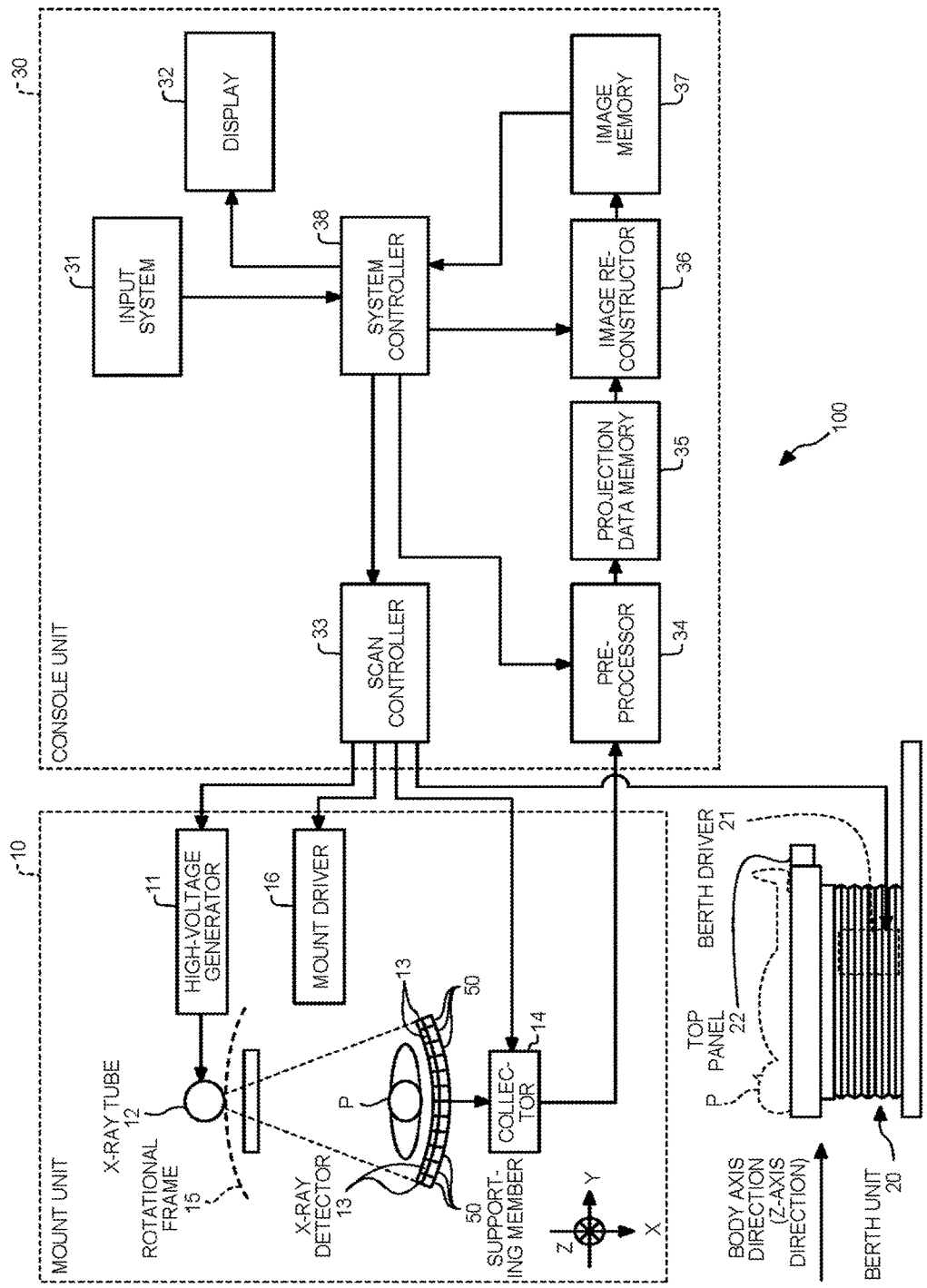
FIG. 1 is a schematic block diagram of an exemplary configuration of an X-ray CT device according to one embodiment.

In exemplary embodiments and modifications described below, same or like elements will be referred to by common reference numerals and a redundant explanation will be partially omitted. Moreover, a portion of an embodiment or a modification can be substituted with a corresponding portion of another embodiment or another modification. Furthermore, the configuration, position, and the like of a portion of an embodiment and a modification are considered to be identical to those of the other embodiments or modifications unless otherwise specified.

Hereinafter, an X-ray computed tomography (CT) device will be described as an example of a photographing device according to an embodiment, with reference to the accompanying drawings.

Embodiment

FIG. 1 is a schematic block diagram of an exemplary configuration of an X-ray CT device 100 according to an embodiment. In FIG. 1, the directions indicated by arrows are defined to be XYZ directions relative to the X-ray CT device 100. The X-ray CT device 100 according to the embodiment includes a mount unit 10, a berth unit 20, and a console unit 30.

The mount unit 10 irradiates a subject P with X-rays to collect X-ray detection data. The mount unit 10 includes a high-voltage generator 11, an X-ray tube 12, a plurality of X-ray detectors 13, a plurality of supporting members 50, a collector 14, a rotational frame 15, and a mount driver 16.

The high-voltage generator 11 generates a high voltage and supplies it to the X-ray tube 12. Herein, the X-ray tube 12 is a vacuum tube that generates X-rays with the high voltage supplied from the high-voltage generator 11. The X-rays generated by the X-ray tube 12 irradiates the subject P.

The X-ray detectors 13 detect the X-rays that are irradiated from the X-ray tube 12 through the subject P. The X-rays are an example of electromagnetic waves. The X-ray detectors 13 represent, for example, two-dimensional array detectors in which a plurality of X-ray detector elements (hereinafter, referred to simply as detector elements) are arranged in a reticular pattern. In the reticular detector element arrays, the direction corresponding to the body axis of the subject P is referred to as slice direction, and the direction perpendicular to the slice direction is referred to as channel direction. Meanwhile, the two-dimensional array structure of the X-ray detectors 13 should not be limited to a flat structure and can be a curved structure.

The supporting members 50 are adapted to support the X-ray detectors 13. Herein, each supporting member 50 supports one or more X-ray detectors 13. The supporting members 50 include, for example, a metallic material such as aluminum or iron. Moreover, the supporting members 50 are cylindrically arranged adjacent to each other. In the cylindrical arrangement the direction in which the supporting members 50 extend is defined to be circumferential direction. The central axis or Z direction of the cylindrical arrangement is defined to be axis direction along an axis of the cylindrical arrangement. The direction that radially extends from the central axis of the cylindrical arrangement is defined to be radial direction. The X-ray tube 12 is disposed on the central axis of the cylinder. The positions of the cylindrically arranged supporting members 50 are mount positions, defined positions, or use positions. The supporting members 50 are held on the rotational frame 15 in a direct or indirect manner along with the X-ray detectors 13. Thus, the supporting members 50 rotate around the Z axis along with the rotational frame 15. Herein, the positions of the supporting members 50 while the X-ray tube 12 is along the X axis on the rotational frame 15 are defined to be central position. The supporting members 50 and the X-ray detectors 13 supported by the supporting members 50 are individually detachably incorporated in the rotational frame 15. When moved in the Z-axis direction, the supporting members 50 are individually detachable from the rest of the supporting members 50 incorporated in the rotational frame 15.

The rotational frame 15 is formed as an annular frame. The rotational frame 15 supports the X-ray tube 12 and the supporting members 50 supporting the X-ray detectors 13 in such a manner that the X-ray tube 12 and the supporting members 50 oppose each other across the subject P. The mount driver 16 is adapted to rotate the X-ray tube 12 and the X-ray detectors 13 on a circular path around the subject P by rotating the rotational frame 15.

The collector 14 collects X-ray signals detected by the X-ray detectors 13, generates data of digital signals (X-ray detection data), and sends the X-ray detection data to the console unit 30. The collector 14 includes a plurality of DAS (Data Acquisition System) chips. For example, the DAS chips amplify or A/D convert the respective X-ray signals detected by the detector elements of the X-ray detectors 13, to generate X-ray detection data. Then, the DAS chips send the X-ray detection data to the console unit 30. Meanwhile, the X-ray detectors 13 and the collector 14 are included in an X-ray detector. Moreover, the X-ray detectors 13 can be either direct detectors or indirect detectors.

The berth unit 20 is a unit on which the subject P lies down and includes a top panel 22 and a berth driver 21 as illustrated in FIG. 1. The top panel 22 is a bed on which the subject lies down. The berth driver 21 moves the top panel 22 along the body axis (Z-axis direction) of the subject P to move the subject P to inside the rotational frame 15.

The console unit 30 receives an operation by an operator with respect to the X-ray CT device 100 as well as reconstructs tomographic image data and volume data from the X-ray detection data generated by the mount unit 10. As illustrated in FIG. 1, the console unit 30 includes an input system 31, a display 32, a scan controller 33, a preprocessor 34, a projection data memory 35, an image reconstructor 36, an image memory 37, and a system controller 38.

The input system 31 includes a mouse, a keyboard, buttons, a trackball, and a joystick that are manipulated by an operator including a doctor or a radiographer to input various kinds of commands; and transfers the received commands from the operator to the later-described system controller 38.

The display 32 includes a monitor for displaying a graphic user interface (GUI) that enables the operator to input various instructions via the input system 31 and for displaying images stored in the later-described image memory 37.

The scan controller 33 controls the operations of the high-voltage generator 11, the mount driver 16, the collector 14, and the berth driver 21. Thereby, the scan controller 33 controls the X-ray scanning of the subject P in the mount unit 10 and collection and data processing of the X-ray detection data.

Specifically, the scan controller 33 performs X-ray scanning by controlling the X-ray tube 12 to emit X-rays in a continuous or intermittent manner while rotating the rotational frame 15. For example, the scan controller 33 performs helical scanning of the subject P while continuously rotating the rotating frame 15 and moving the top panel 22 or performs conventional scanning in which of the subject P while rotating the rotational frame 15 once or continuously and securing the position of the subject P.

The preprocessor 34 generates projection data by performing correction such as logarithmic conversion, offset correction, sensitivity correction, or beam hardening correction to the X-ray detection data sent from the collector 14. The projection data memory 35 stores the projection data generated by the preprocessor 34.

The image reconstructor 36 generates various kinds of images from the projection data stored in the projection data memory 35 and stores the images in the image memory 37. For example, the image reconstructor 36 reconstructs an X-ray CT image by back projection method (for example, filtered back projection (FBP)) and stores the reconstructed X-ray CT image in the image memory 37.

The system controller 38 controls the operations of the mount unit 10, the berth unit 20, and the console unit 30 to control the overall operation of the X-ray CT device 100. Specifically, the system controller 38 controls the scan controller 33 so as to control the collection of the X-ray detection data group by the mount unit 10 and the berth unit 20. Moreover, the system controller 38 controls the preprocessor 34 and the image reconstructor 36 so as to control the image processing of the console unit 30. Furthermore, the system controller 38 controls the display 32 to display various images stored in the image memory 37.

Figure 2:
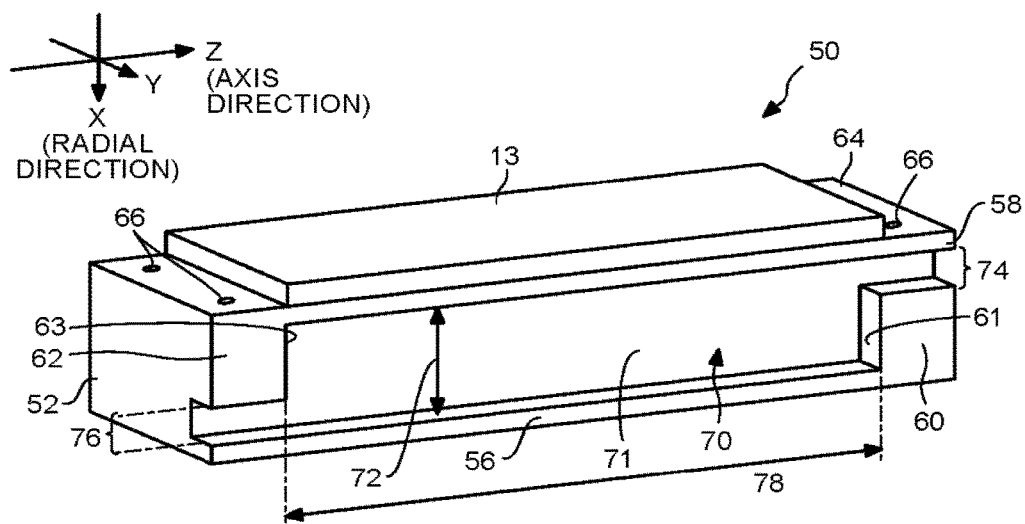
FIGS. 2 and 3 are exemplary schematic perspective views of an X-ray detector and a supporting member according to the embodiment.
Figure 3:
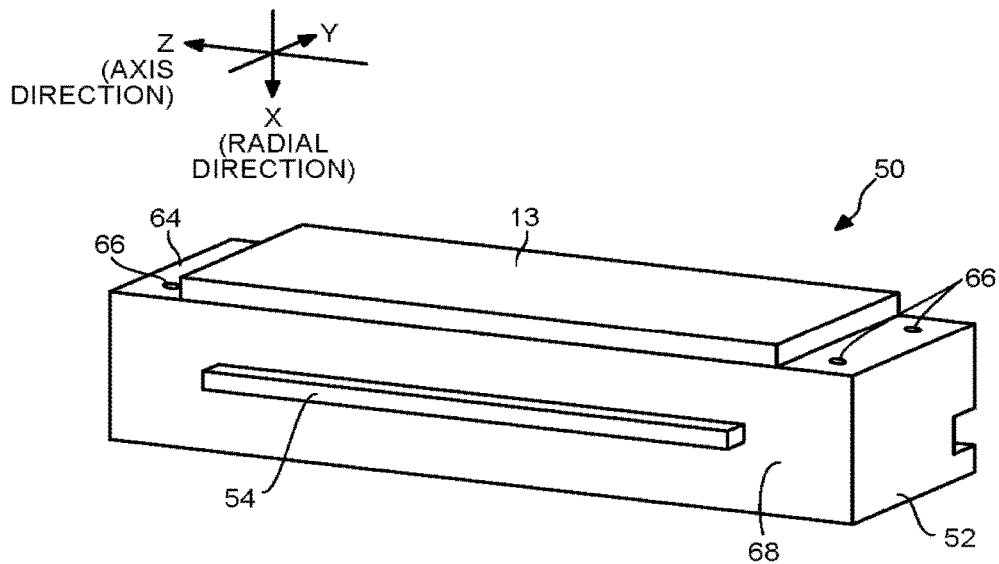

FIGS. 2 and 3 are schematic perspective views of the X-ray detector and the supporting member according to the embodiment by way of example. As described earlier, the supporting members 50 are cylindrically arranged. FIG. 2 is a perspective view of the supporting member 50 from the positive Y side. FIG. 3 is a perspective view of the supporting member 50 from the negative Y side.

As illustrated in FIGS. 2 and 3, the supporting member 50 includes a body 52, a first protrusion 54, two second protrusions 56 and 58, a first restrictor 60, and a second restrictor 62. Herein, the first protrusion 54, the two second protrusions 56 and 58, the first restrictor 60, and the second restrictor 62 are integrally provided on the body 52.

The body 52 has a substantially cuboid shape. The body includes a face 64 serving as a support face for supporting the X-ray detectors 13. The face 64 is one of the faces of the body 52 closer to the center of the radial direction. The face 64 includes a plurality (for example, four) of mounting holes 66 into which captive screws are inserted for the purpose of directly or indirectly fixing the supporting member 50 to the rotational frame 15.

The first protrusion 54 is provided on one of the side faces of the supporting member 50 in the circumferential direction. That is, the first protrusion 54 is provided on a side face 68 of the body 52 in the circumferential direction. The first protrusion 54 protrudes from the side face 68 in the circumferential direction. The first protrusion 54 is provided at the center of the side face 68 in the radial direction. However, the position of the first protrusion 54 should not be limited to the center of the side face 68 in the radial direction and can be suitably changed according to the positions of the second protrusions 56 and 58 as described later. The first protrusion 54 has a cuboid shape and axially extends. Moreover, the length of the first protrusion 54 is shorter than the axial length of the body 52. Herein, the first protrusion 54 is provided at the axial center of the body 52. In other words, both axial ends of the first protrusion 54 are spaced from the axial ends of the side face 68 of the body 52. Meanwhile, the position of the first protrusion 54 should not be limited to the axial center of the body 52 and can be suitably changed according to the positions of the first restrictor 60 and the second restrictor 62 as described later.

The two second protrusions 56 and 58 are provided on the other side face 70 of the supporting member 50 in the circumferential direction. That is, the two second protrusions 56 and 58 are provided on the side face 70 of the body 52 in the circumferential direction. The two second protrusions 56 and 58 are provided on the side face 70 opposite the side face 68 on which the first protrusion 54 is provided. The second protrusions 56 and 58 have a substantially same length as the length of the side face 70 in the axis direction. In other words, the second protrusions 56 and 58 axially extend over the substantially entire length of the side face 70. The second protrusions 56 and 58 protrude from the side face 70 in the circumferential direction. The protrusion amount of the second protrusions 56 and 58 is smaller than that of the first protrusion 54. Thus, even when the first protrusion 54 contacts a side face of the body 52 of the neighboring supporting member 50, the second protrusions 56 and 58 do not. Meanwhile, the protruding in the circumferential direction refers to protruding toward the neighboring supporting member 50. In this case, the protrusion occurs from the side face 70.

For attaching or detaching an intended supporting member 50 to or from the rotational frame 15 by moving the supporting member 50 in the axis direction, the two second protrusions 56 and 58 are guided in the axis direction by the attached first protrusion 54 of the neighboring supporting member 50 while the first protrusion 54 is guided in the axis direction by the second protrusions 56 and 58 of the attached neighboring supporting member 50. In other words, when the neighboring supporting member 50 is moved in the axis direction to be detached or attached from or to the rotational frame 15, the two second protrusions 56 and 58 of the attached supporting member 50 work to guide the first protrusion 54 of the neighboring supporting member 50 in the axis direction. Moreover, when the neighboring supporting member 50 is moved in the axis direction to be detached from or attached to the rotational frame 15, the first protrusion 54 of the attached supporting member 50 works to guide the second protrusions 56 and 58 of the neighboring supporting member 50 in the axis direction. Thus, the first protrusion 54 functions as a mover or a slider that slides the second protrusions 56 and 58. On the other hand, the second protrusions 56 and 58 function as a guide for the first protrusion 54. Further, the second protrusions 56 and 58 form a crank-like depression 71 that is equivalent to the path or the trajectory of the moving first protrusion 54 functioning as a mover. Thus, in the present embodiment, a mover in the form of the first protrusion 54 is provided on the side face 68 while the second protrusions 56 and 58 form a path on the other side face 70 in the circumferential direction for relatively moving the first protrusion 54 as a mover with respect to the neighboring supporting member 50.

The second protrusion 56 is provided at one radial end of the side face 70 of the body 52. An example of the one end is an outside end in the radial direction, that is, an end (opposite the central side on which the X-ray tube 12 is located). The other second protrusion 58 is provided at the other radial end of the side face 70 of the body 52. An example of the other end is an inside end in the radial direction (on the central side on which the X-ray tube 12 is located). The sum of the radial widths of the second protrusions 56 and 58 is shorter than the radial length of the side face 70 of the body 52. Thus, the second protrusions 56 and 58 are arranged with a gap 72 in the radial direction. Herein, the gap 72 between the two second protrusions 56 and 58 is greater than the radial width of the first protrusion 54. Hence, the first protrusion 54 can move in the radial direction in-between the two second protrusions 56 and 58.

The first restrictor 60 is provided at one axial end of the side face 70 of the supporting member 50. An example of the one axial end is an end in the positive Z direction. The first restrictor 60 protrudes from the side face 70. Moreover, the first restrictor 60 is provided in continuation with the second protrusion 56. Furthermore, the first restrictor 60 extends from the second protrusion 56 inward radially. Thus, the first restrictor 60 is formed to protrude in the radial direction from the second protrusion 56. Hence, the first restrictor 60 of each supporting member 50 is guided by the second protrusion 56 of the same supporting member 50 to contact with the first protrusion 54 of the neighboring supporting member 50 moving in the positive Z direction. As a result, the first restrictor 60 restricts at least either the axial (positive Z direction) or radial movement of the first protrusion 54 of the neighboring supporting member 50. The first restrictor 60 and the second protrusion 58 are provided with a gap 74 in the radial direction. The gap 74 is greater than the width of the first-type protrusion 54 and smaller than the gap 72 in the radial direction. Thereby, the gap 74 enables the first protrusion 54 to move between the first restrictor 60 and the second protrusion 58 in the axis direction but more largely restricts the radial movement of the first protrusion 54 than the gap 72. A face 61 of the first restrictor 60 in contact with the first protrusion 54 of the neighboring supporting member 50 radially extends. Hence, the face 61 of the first restrictor 60 works to guide the contacting first protrusion 54 in the radial direction.

The second restrictor 62 is provided on the other axial end of the side face 70 of each supporting member 50. An example of the other axial end is an end in the negative Z direction. The second restrictor 62 protrudes from the side face 70. Moreover, the second restrictor 62 is provided in continuation with the second protrusion 58. Furthermore, the second restrictor 62 extends from the second protrusion 58 outward radially. Thus, the second restrictor 62 is formed to protrude in the radial direction from the second protrusion 58. Hence, the second restrictor 62 of each supporting member 50 is guided by the second protrusion 58 of the same supporting member 50 to contact with the first protrusion 54 of the neighboring supporting member 50 moving in the negative Z direction. As a result, the second restrictor 62 restricts at least either the axial (negative Z direction) or radial movement of the first protrusion 54 of the neighboring supporting member 50. The second restrictor 62 is spaced from the second protrusion 56 with a gap 76 in the radial direction. The gap 76 is spaced from the gap 74 in the radial direction. Moreover, the gap 76 is greater than the width of the first protrusion 54 and smaller than the gap 72 in the radial direction. As a result, the gap 74 enables the first protrusion 54 to move between the second restrictor 62 and the second protrusion 56 in the axis direction but more largely restricts the movement of the first protrusion 54 in the radial direction than the gap 72. A face 63 of the second restrictor 62 in contact with the first protrusion 54 of the neighboring supporting member 50 extends in the radial direction. Hence, the face 63 of the second restrictor 62 works to guide the contacting first protrusion 54 in the radial direction. The two second protrusions 56 and 58, the first restrictor 60, and the second restrictor 62 can be arranged symmetrically with respect to the center of the side face 70.

As described above, the first restrictor 60 is provided at one axial end (positive Z end) of the supporting member 50 while the second restrictor 62 is provided at the other axial end (negative Z end) of the supporting member 50. Moreover, the sum of the widths of the first restrictor 60 and of the second restrictor 62 in the axis direction is shorter than the length of the supporting member 50 in the axis direction. Thus, the first restrictor 60 and the second restrictor 62 are disposed with a gap 78. Herein, the gap 78 is longer than the length of the first protrusion 54 in the axis direction. Hence, the first protrusion 54 can enter and move in the gap 78 in the radial direction.

Figure 4:
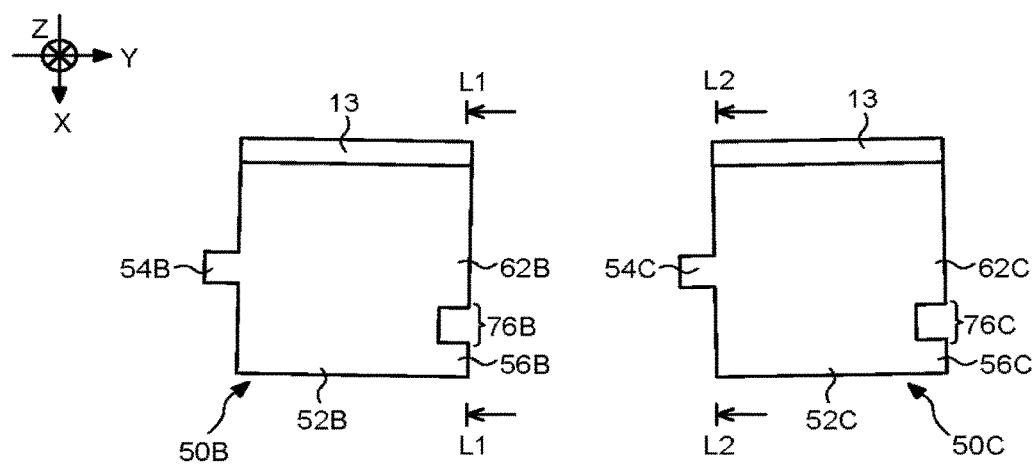
FIGS. 4 to 10 are exemplary schematic diagrams for explaining the process of attaching a supporting member.
Figure 5:
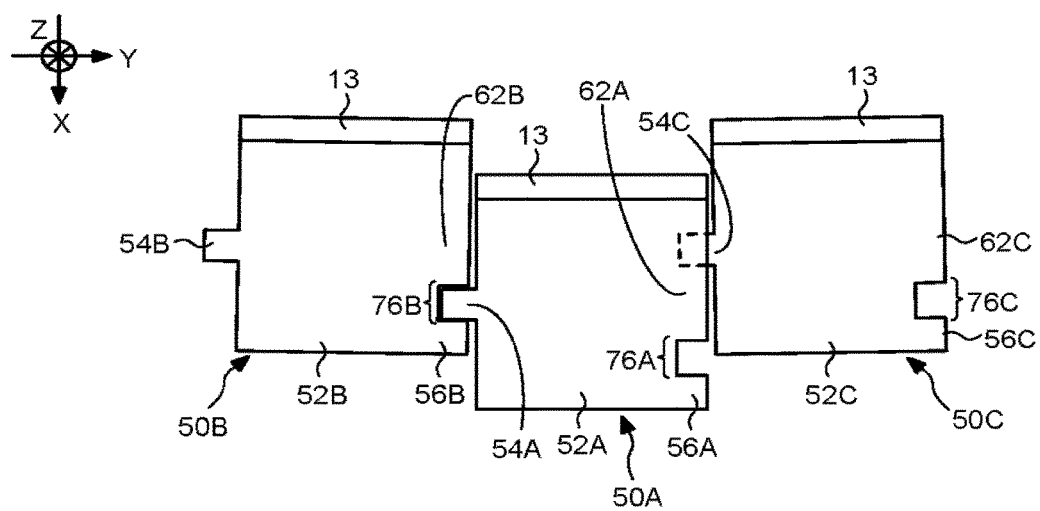
Figure 6:
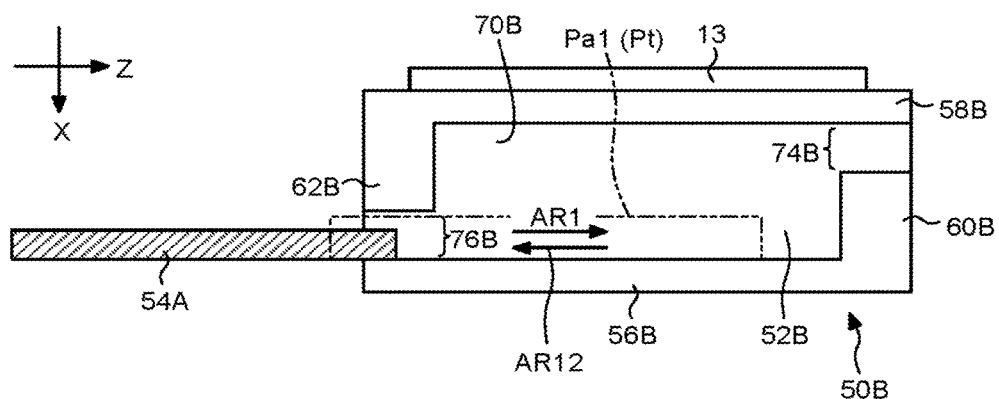
Figure 7:
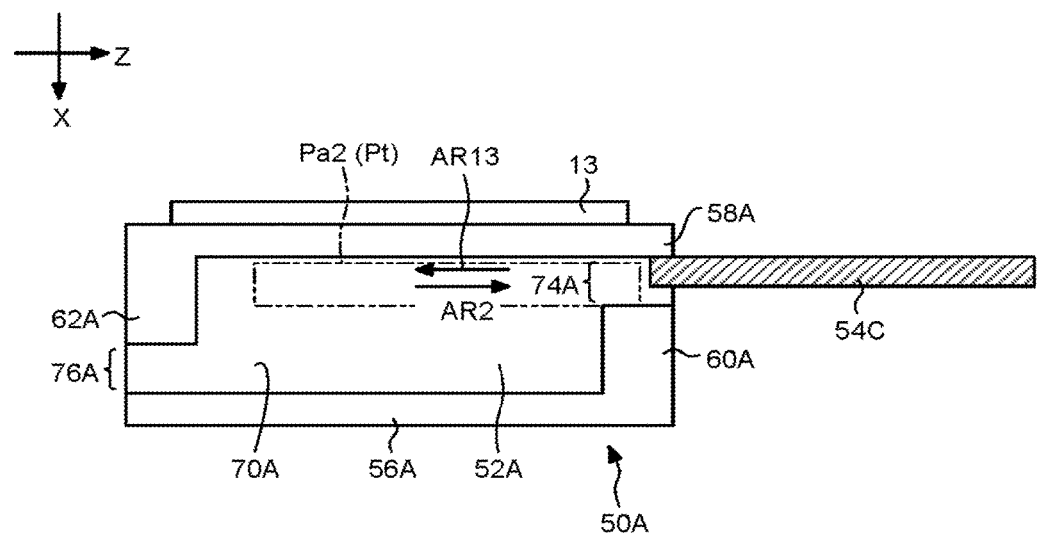
Figure 8:
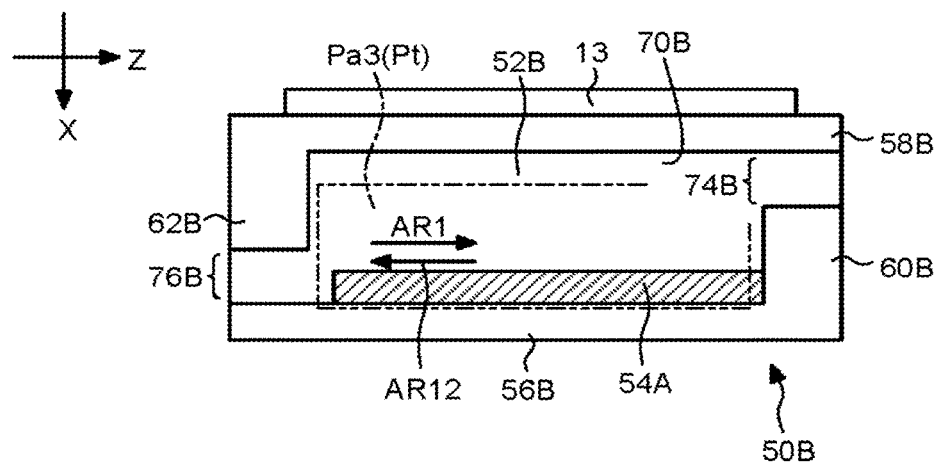
Figure 9:
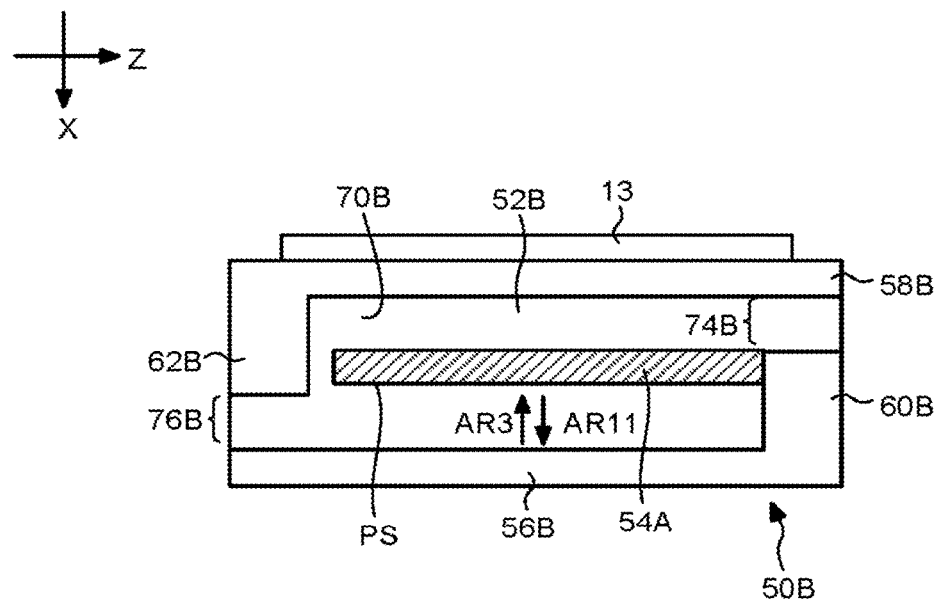
Figure 10:
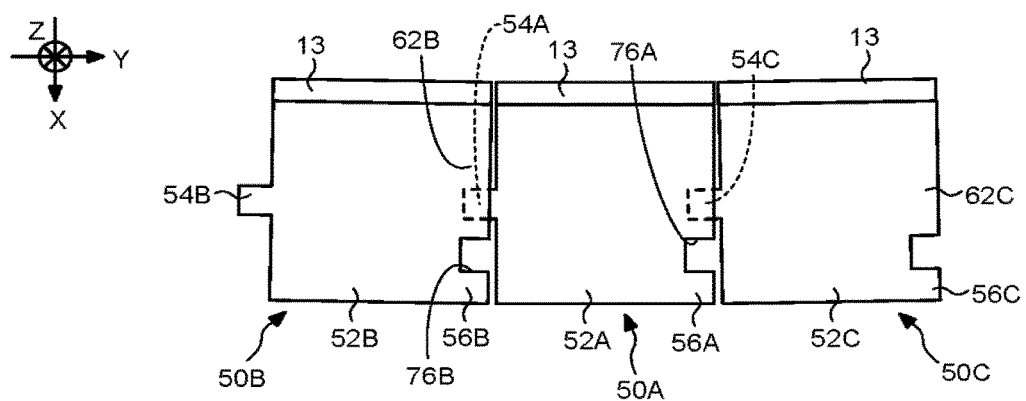

FIGS. 4 to 10 are schematic diagrams for explaining the process of attaching a supporting member. FIGS. 4, 5, and 10 are diagrams of the supporting members 50 when viewed from the negative Z direction. FIGS. 6, 8, and 9 are side views (including cross-sectional views) along a L1-L1 line illustrated in FIG. 4. FIG. 7 is a side view (including cross-sectional view) along a L2-L2 line illustrated in FIG. 4. Herein, supporting members 50B and 50C illustrated in FIG. 4 are already assembled. The process of attaching a supporting member 50A will be described referring to FIG. 5 and subsequent drawings. The supporting members 50A, 50B, and 50C have the same structure as that of the supporting member 50. The respective elements of the supporting members 50A, 50B and 50C are given the reference numerals with characters "A", "B", and "C" added.

As illustrated in FIG. 4, to start with, the supporting member 50A between the supporting members 50B and 50C is in a detached state. Then, the supporting member 50A is attached between the supporting members 50B and 50C.

First, as illustrated in FIGS. 5 and 6, the supporting member 50A is inserted between the supporting members 50B and 50C from the negative Z direction to the positive direction (in the axis direction) indicated by an arrow AR1. Herein, the axis direction also refers to an inserting direction of the supporting member 50A between the neighboring supporting members 50B and 50C. In this state, second protrusions 56B and 58B of the supporting member 50B overlap with a first protrusion 54A of the neighboring supporting member 50A in the radial direction. Here, the supporting member 50A is disposed more outside (opposite the center) in the radial direction than the supporting members 50B and 50C. More specifically, the first protrusion 54A of the supporting member 50A is aligned in the radial direction with a gap 76B between the second protrusion 56B and a second restrictor 62B of the supporting member 50B. Thus, when the supporting member 50A is inserted between the supporting members 50B and 50C, the first protrusion 54A of the supporting member 50A is not restricted from moving in the positive Z direction (the axis direction). That is, the first protrusion 54A of the supporting member 50A is not restricted from relatively moving in the positive Z direction (the axis direction) with respect to the second protrusion 56B and the second restrictor 62B. As illustrated in FIG. 6, the second protrusion 56B and the second restrictor 62B form a first section Pa1 (Pt) of the path for guiding the first protrusion 54A as a mover in the axis direction. The first section Pa1 is an example of a first path. By the first section Pa1, the path of the supporting member 50 when axially moved for attachment or detachment is defined.

Moreover, in FIGS. 5 and 6, the supporting member 50A is disposed more outside than the supporting members 50B and 50C in the radial direction (opposite the center). Hence, the gap between the supporting member 50A and the supporting member 50B (or the supporting member 50C) in the circumferential direction is greater than that when the supporting members are attached (i.e., when the supporting member 50A is disposed at the same position in the radial direction as the supporting members 50B and 50C).

Moreover, as illustrated in FIG. 7, a first protrusion 54C of the supporting member 50C is aligned with a gap 74A between a second protrusion 58A and a first restrictor 60A of the supporting member 50A. Thus, the first protrusion 54C of the supporting member 50C does not restrict the axial movement of the supporting member 50A. As a result, the supporting member 50A can relatively move in the positive Z direction with respect to the supporting member 50C as indicated by an arrow AR2. As illustrated in FIG. 7, the second protrusion 58A and the first restrictor 60A form a second section Pa3 (Pt) of the path for guiding the first protrusion 54C as a mover in the axis direction. The second section Pa2 is an example of a first path. By the first section Pa2, the path of the supporting member 50A when axially moved for attachment is defined.

Then, the supporting member 50A is moved in the positive Z direction while the first protrusion 54A is guided by the second protrusion 56B of the supporting member 50B in the axis direction. When the supporting member 50A moves for a certain distance in the positive Z direction, the first protrusion 54A of the supporting member 50A makes contact with a first restrictor 60B of the supporting member 50B as illustrated in FIG. 8. Thereby, the movement of the supporting member 50A in the positive Z direction is restricted. However, the first protrusion 54A of the supporting member 50A can move between the two second protrusions 56B and 58B toward the radial center.

Subsequently, as illustrated in FIG. 9, the supporting member 50A is moved toward the radial center as indicated by an arrow AR3. That is, with respect to the supporting members 50B and 50C, the supporting member 50A is relatively moved toward the radial center as indicated by the arrow AR3. Then, the supporting member 50A is positioned with a pin (not illustrated) and fixed on a body 52A with captive screws inserted into the mounting holes 66 thereof. Thereby, as illustrated in FIG. 10, the supporting members 50A, 50B, and 50C are cylindrically arranged. This completes the process of attaching the supporting member 50A. As illustrated in FIG. 8, the first restrictor 60B and the second restrictor 62B form a third section Pa3 (Pt) of the path for guiding the first protrusion 54A as a mover in the radial direction. The third section Pa3 is an example of a second path. The path of the supporting member 50A when axially moved for attachment is defined by the third section Pa3 (Pt). The third section Pa3 is provided in-between the first section Pa1 and the second section Pa2. Moreover, the first section Pa1, the second section Pa2, and the third section Pa3 are provided between the second protrusions 56 and 58. Furthermore, a position Ps of the first protrusion 54A as illustrated in FIG. 9 represents the position at which the supporting member 50A is assembled. Herein, the position Ps is the center of the path Pt and can be referred to as an assembly position, a predetermined position, a mounting position, or a use position. When viewed from the circumferential direction, the path Pt is laid in point symmetric to the position Ps.

The process of detaching the supporting member 50 is a reverse process of attaching the supporting member 50. That is, in the detaching process, the supporting member 50A in FIGS. 9 and 10 relatively moves with respect to the supporting members 50B and 50C radially outward as indicated by an arrow AR11. By this movement, the X-ray detectors 13 of the supporting member 50A are moved from a close position to a remote position relative to the supporting members 50B and 50C in the circumferential direction as illustrated in FIGS. 9 and 10. Thus, the radially outward moving direction can also be called a remote direction. By such movement, the first protrusion 54A of the supporting member 50A makes contact with the second protrusion 56B of the supporting member 50B as illustrated in FIG. 8. Then, with respect to the supporting members 50B and 50C, the supporting member 50A relative moves in the negative Z direction as indicated by an arrow AR12 in FIG. 8. In this state as illustrated in FIG. 7, the first protrusion 54C of the supporting member 50C is positioned between the second protrusion 58A and the first restrictor 60A. Hence, the supporting member 50A can move in the negative Z direction (axis direction) indicated by an arrow AR13. Then, as illustrated in FIG. 6, the supporting member 50A is further moved in the negative Z direction indicated by the arrow AR12 and detached from the supporting members 50B and 50C.

Meanwhile, the attaching and detaching processes for the neighboring supporting members 50B and 50C are performed in the same manner as that for the supporting member 50A.

As described earlier, the two second protrusions 56 and 58 of the supporting members 50 are spaced with the gap 72 greater than the width of the first-type protrusion 54 in the radial direction. Thus, the supporting member 50B guides the first protrusion 54A of the neighboring supporting member 50A in the axis direction which is the moving direction during assembly, and at the same time allows the first protrusion 54A to move in the radial direction. As a result, the supporting member 50A can be assembled from the outside of the assembled supporting members 50B and 50C in the radial direction. Hence, the supporting member 50A can be assembled with an increased gap between the supporting members 50B and 50C. Thereby, while moving in the axis direction, the X-ray detectors 13 of the supporting member 50A can be prevented from contacting the neighboring supporting members 50B and 50C as well as the X-ray detectors 13 of the supporting members 50B and 50C.

Moreover, when the supporting member 50A moves in the circumferential direction, the first protrusion 54A of the supporting member 50A makes contact with a side face 70B of a body 52B of the supporting member 50B or a side face 70A of the body 52A of the supporting member 50A makes contact with the first protrusion 54C of the supporting member 50C, making it possible to restrict the movement of the supporting member 50A in the circumferential direction. As a result, the X-ray detectors 13 of the supporting member 50A can be prevented from contacting the neighboring supporting members 50B and 50C as well as the X-ray detectors 13 of the supporting members 50B and 50C.

The first restrictor 60B of the supporting member 50B restricts the movement of the supporting member 50A in the positive Z direction (i.e., moving direction along the axis during assembly). As a result, the supporting member 50A can be prevented from passing an intended assembly position in the positive Z direction, and hence can be correctly positioned with ease.

The second protrusion 56B and the second restrictor 62B of the supporting member 50B restrict the movement of the supporting member 50A in the radial direction. As a result, the supporting member 50A can be prevented from moving in the radial direction and falling down.

During the attaching or detaching process, when the supporting member 50A rotates around the axis, the first protrusion 54A of the supporting member 50A is restricted from rotating by either of the second protrusion 56B and the second restrictor 62B of the supporting member 50B, and either of the second protrusion 58A and the first restrictor 60A of the supporting member 50A is restricted from rotating by the first protrusion 54C of the supporting member 50C. As a result, the rotation of the supporting member 50A around the axis can be inhibited.

During the attaching or detaching process, when the supporting member 50A rotates around the circumference, the first protrusion 54A of the supporting member 50A is restricted from rotating by either of the second protrusion 56B and the second restrictor 62B of the supporting member 50B, and the second protrusion 58A of the supporting member 50A is restricted from rotating by the first protrusion 54C of the supporting member 50C. As a result, the supporting member 50A can be inhibited from rotating around the circumference.

The first section Pa1 formed by the second restrictor 62 and the second protrusion 56 can guide the relative movement of the supporting member 50A to be attached and the neighboring supporting member 50B in the axis direction.

The second section Pa2 formed by the first restrictor 60 and the second protrusion 58 can guide the relative movement of the supporting member 50A to be attached and the neighboring supporting member 50C in the axis direction.

Each supporting member 50 includes the first protrusion 54 as a mover on the side face 68 and the crank-like depression 71 serving as a movement path on the side face 70. Hence, the supporting members 50 having the same shape can be arranged detachably and attachably with respect to each other.

First Modification

Figure 11:
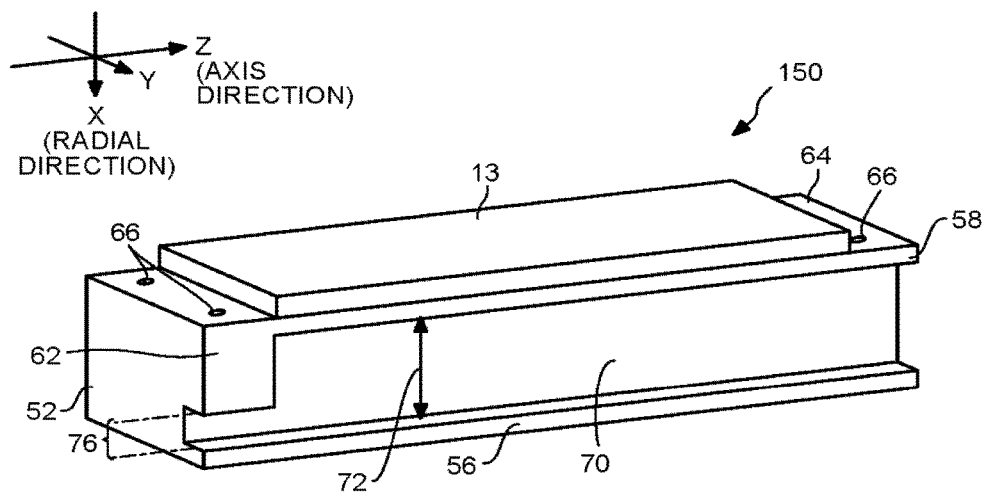
FIG. 11 is a schematic perspective view of an example of a supporting member according to a first modification.

FIG. 11 is a schematic perspective view of an example of a supporting member according to a first modification. As illustrated in FIG. 11, a supporting member 150 includes the body 52, the first protrusion 54, the second protrusions 56 and 58, and the second restrictor 62. In other words, the supporting member 150 is configured to exclude the first restrictor 60 of the supporting member 50.

Second Modification

Figure 12:
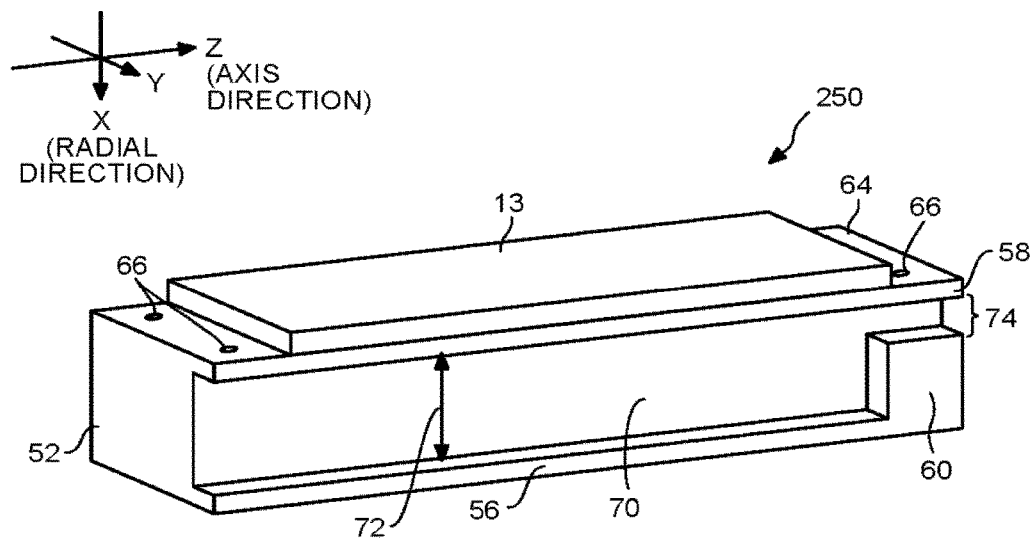
FIG. 12 is a schematic perspective view of an example of a supporting member according to a second modification.

FIG. 12 is a schematic perspective view of an example of a supporting member according to a second modification. As illustrated in FIG. 12, a supporting member 250 includes the body 52, the first protrusion 54, the second protrusions 56 and 58, and the first restrictor 60. In other words, the supporting member 250 is configured to exclude the second restrictor 62 of the supporting member 50.

Third Modification

Figure 13:
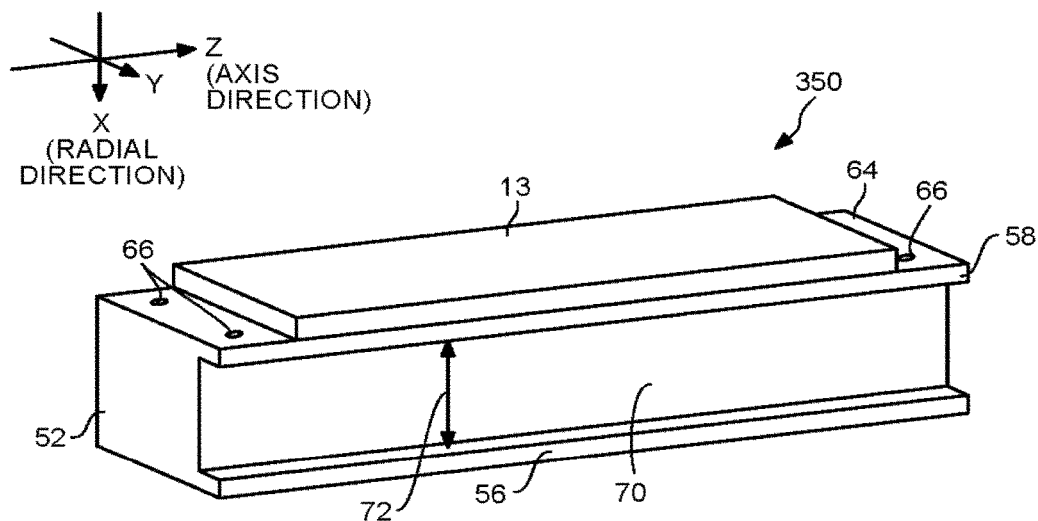
FIGS. 13 and 14 are schematic perspective views of examples of a supporting member according to a third modification.
Figure 14:
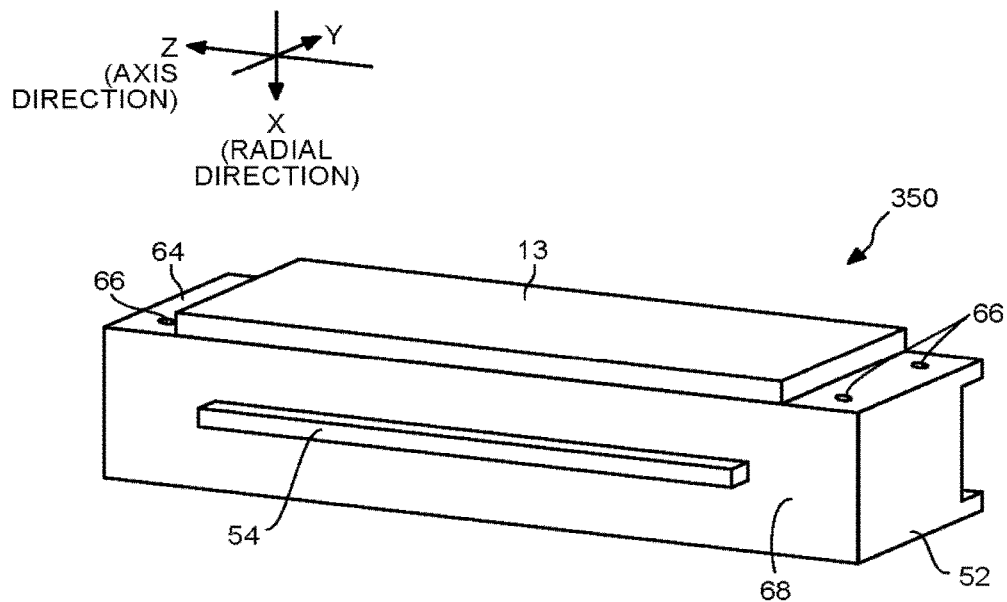

FIGS. 13 and 14 are schematic perspective views of examples of a supporting member according to a third modification. FIG. 13 is a perspective view of a supporting member 350 from the positive Y side. FIG. 14 is a perspective view of the supporting member 350 from the negative Y side.

As illustrated in FIGS. 13 and 14, the supporting member 350 includes the body 52, the first protrusion 54, and the second protrusions 56 and 58. In other words, the supporting member 350 is configured to exclude the first restrictor 60 and the second restrictor 62 of the supporting member 50.

Figure 15:
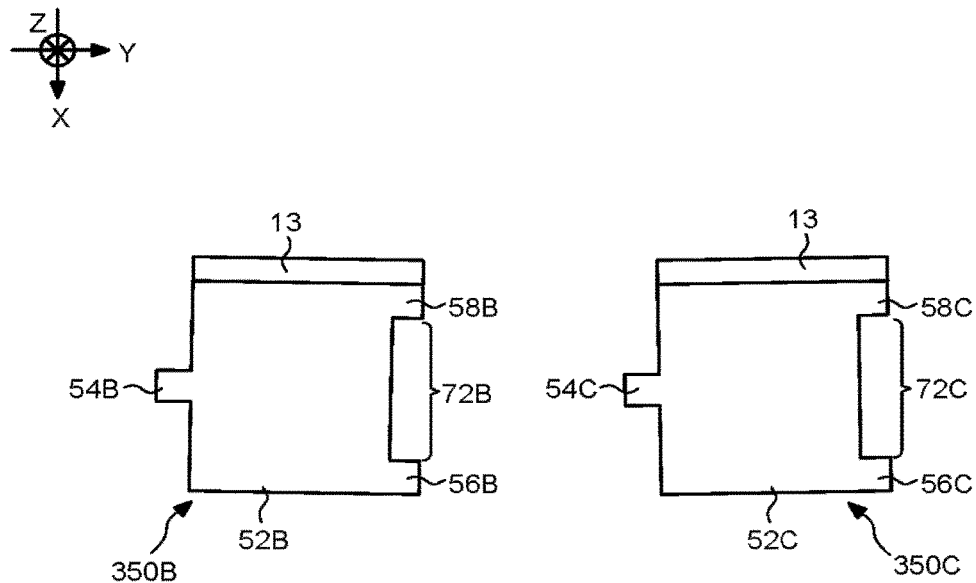
FIGS. 15 to 17 are exemplary schematic diagrams for explaining the process of attaching the supporting member according to the third modification.
Figure 16:
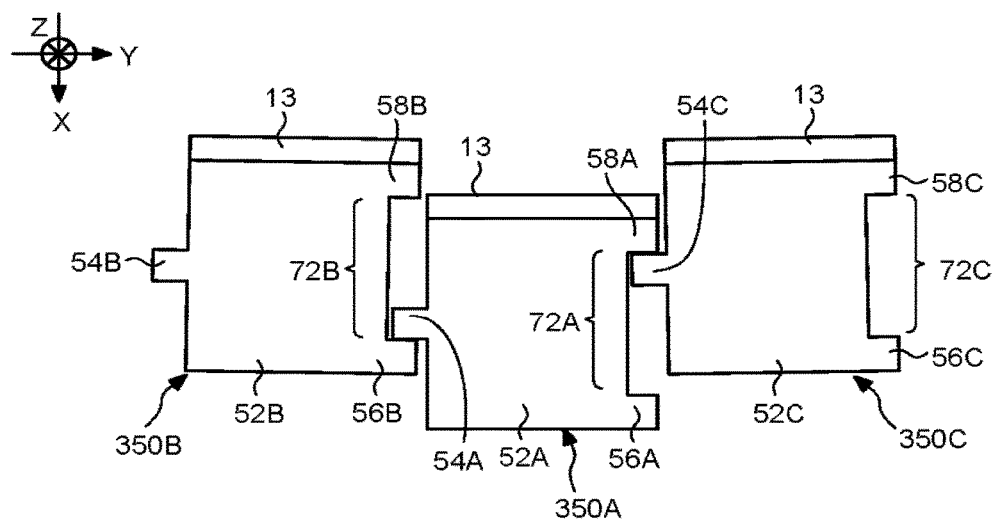
Figure 17:
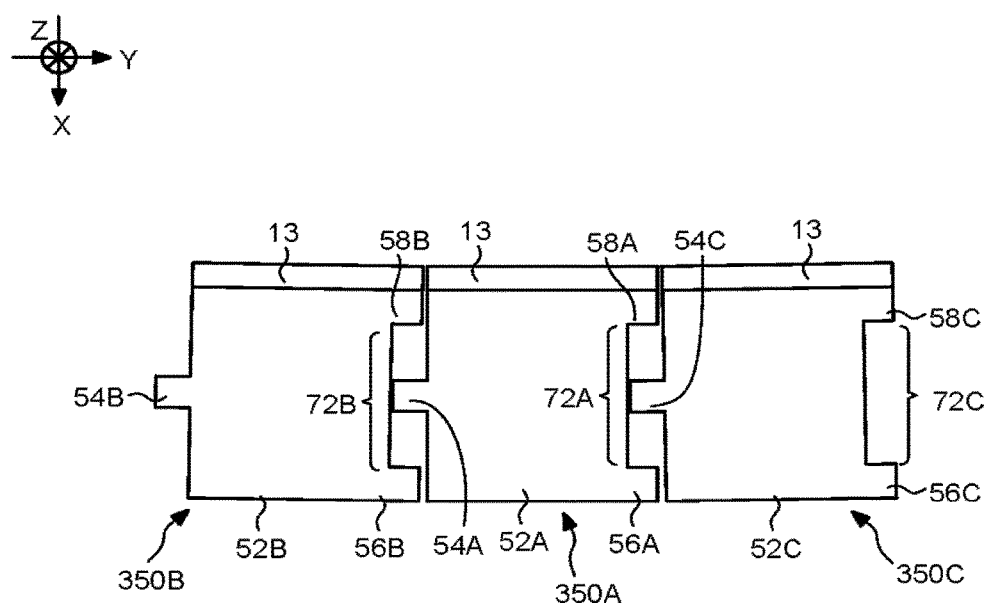

FIGS. 15 to 17 are exemplary schematic diagrams for explaining the supporting member attaching process according to the third modification. FIGS. 15 to 17 are diagrams illustrating the supporting member 350 when viewed from the negative Z direction. Herein, supporting members 350B and 350C illustrated in FIG. 15 are already assembled. The process of attaching a supporting member 350A will be described referring to FIGS. 16 and 17. The supporting members 350A, 350B, and 350C have the same configuration to the configuration of the supporting member 350.

As illustrated in FIG. 15, to start with, the supporting member 350A between the supporting members 350B and 350C is in a detached state. Then, the supporting member 350A is attached between the supporting members 350B and 350C.

First, as illustrated in FIG. 16, the supporting member 350A is inserted between the supporting members 350B and 350C from the negative Z direction to the positive Z direction. Herein, the supporting member 350A is disposed more outside (opposite the center) than the supporting members 350B and 350C in the radial direction. More specifically, the first protrusion 54A of the supporting member 350A is aligned in the radial direction with a gap 72B between the second protrusions 56B and 58B of the supporting member 350B. Thus, when the supporting member 350A is inserted in-between the supporting members 350B and 350C, the axial movement of the first protrusion 54A of the supporting member 350A is not restricted.

The first protrusion 54C of the supporting member 350C is aligned in the radial direction with a gap 71A between second protrusions 56A and 58A of the supporting member 350A. As a result, as illustrated in FIG. 16, when the supporting member 350A moves downward, the first protrusion 54A of the supporting member 350A makes contact with the second protrusion 56B of the supporting member 350B or the first protrusion 54C of the supporting member 350C makes contact with the second protrusion 58A of the supporting member 350A. Thereby, the downward movement of the supporting member 350A is restricted.

Subsequently, the supporting member 350A is inserted to a predetermined position in the Z direction and moved toward the radial center as illustrated in FIG. 17. In this state the supporting member 350A is fixed by inserting captive screws into the mounting holes 66.

Fourth Modification

Figure 18:
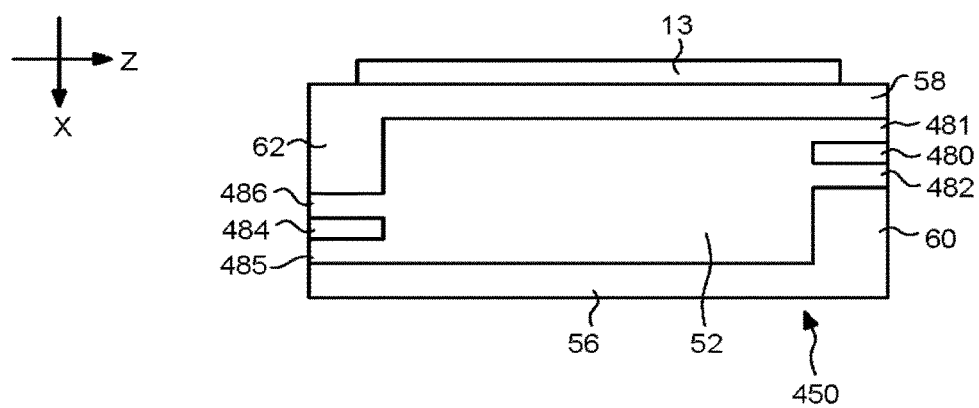
FIG. 18 is a schematic side view of a supporting member according to a fourth modification.
Figure 19:
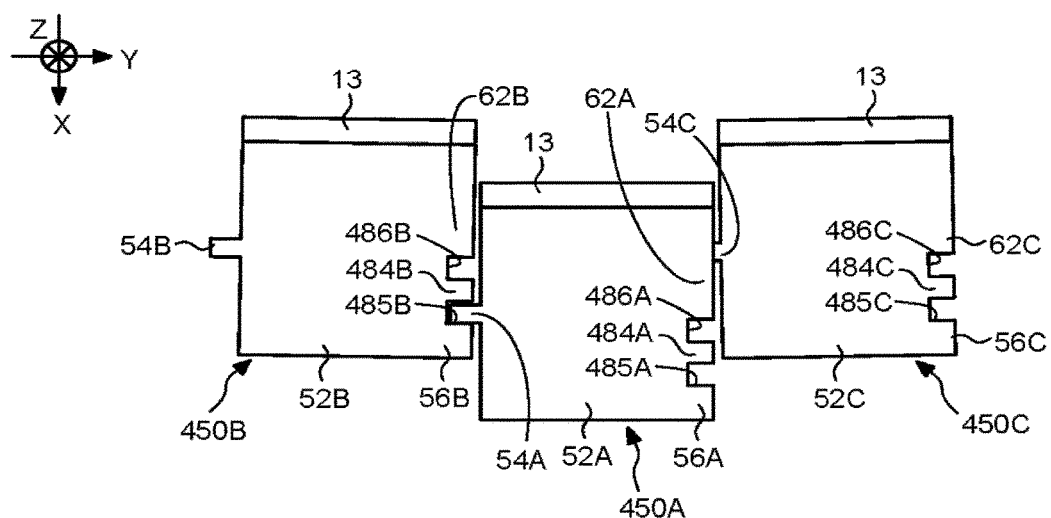
FIGS. 19 and 20 are exemplary schematic diagrams for explaining the process of attaching the supporting member according to the fourth modification.
Figure 20:
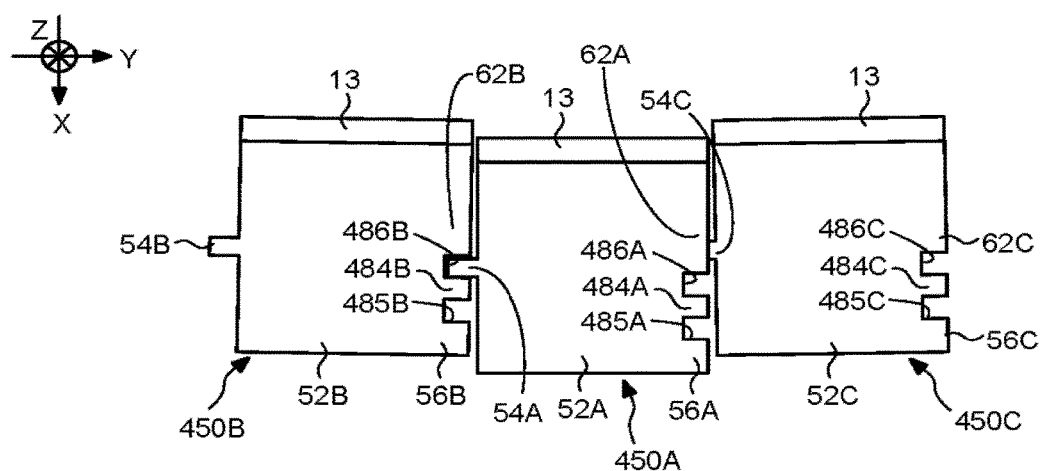

FIG. 18 is a schematic side view of an example of a supporting member according to a fourth modification. Herein, FIG. 18 is a schematic side view of the supporting member from the side face 70. FIGS. 19 and 20 are schematic diagrams for explaining the supporting member attaching process according to the fourth modification.

As illustrated in FIG. 18, a supporting member 450 includes a first divider 480 and a second divider 484 on the side face 70 of the body 52. The elements on the side face 68 of the supporting member 450 are identical to those of the supporting member 50. Hence, a description thereof is omitted.

The first divider 480 protrudes in the circumferential direction from the side face 70. Moreover, the first divider 480 is provided in-between the second protrusion 58 and the first restrictor 60. In other words, the first divider 480 divides the gap between the second protrusion 58 and the first restrictor 60. As a result, a gap 481 occurs between the first divider 480 and the second protrusion 58 while a gap 482 occurs between the first divider 480 and the first restrictor 60.

The second divider 484 protrudes in the circumferential direction from the side face 70. Moreover, the second divider 484 is provided in-between the second protrusion 56 and the second restrictor 62. In other words, the second divider 484 divides the gap between the second protrusion 56 and the second restrictor 62. As a result, a gap 485 occurs between the second divider 484 and the second protrusion 56 while a gap 486 occurs between the second divider 484 and the second restrictor 62. Herein, the gaps 481, 482, 485, and 486 have a greater width than the first protrusion 54 in the radial direction. Thus, the first protrusion 54 can move through any of the gaps 481, 482, 485, and 486.

for attaching a supporting member 450A in-between supporting members 450B and 450C, the first protrusion 54A can be inserted into a gap 485B as illustrated in FIG. 19 or into a gap 486B as illustrated in FIG. 20.

Fifth Modification

Figure 21:
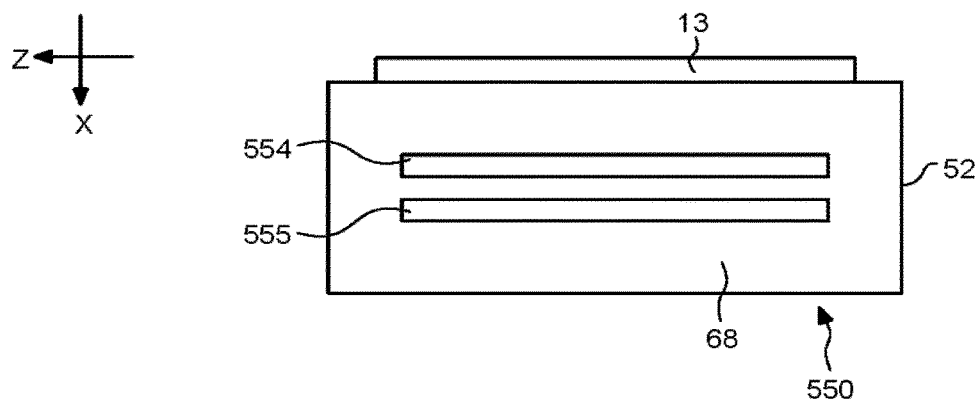
FIG. 21 is a schematic side view of an example of a supporting member according to a fifth modification.
Figure 22:
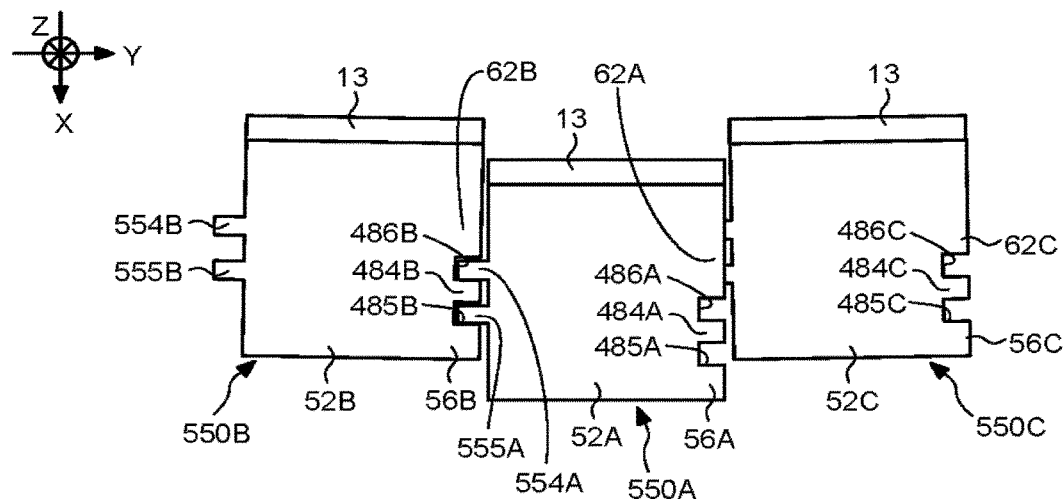
FIG. 22 is an exemplary schematic diagram for explaining the process of attaching the supporting member according to the fifth modification.

FIG. 21 is a schematic side view of an example of a supporting member according to a fifth modification. Herein, FIG. 21 is a side view of the supporting member from the side face 68. FIG. 22 is an exemplary schematic diagram for explaining the supporting member attaching process according to the fifth modification.

As illustrated in FIG. 21, a supporting member 550 includes two first protrusions 554 and 555 on the side face 68 of the body 52. The elements on the side face 70 of the supporting member 550 are identical to those of the supporting member 450. Hence, a description thereof is omitted.

The two first protrusions 554 and 555 are aligned in the radial direction. The gap between the first protrusions 554 and 555 is greater than the width of the first divider 480 and the second divider 484 in the radial direction. Moreover, the width of the first protrusions 554 and 555 is smaller than the width of the gaps 481, 482, 485, and 486 in the radial direction. Thus, for attaching a supporting member 550A between supporting members 550B and 550C, first protrusions 554A and 555A can be inserted into the gaps 486B and 485B, respectively, as illustrated in FIG. 22.

Sixth Modification

Figure 23:
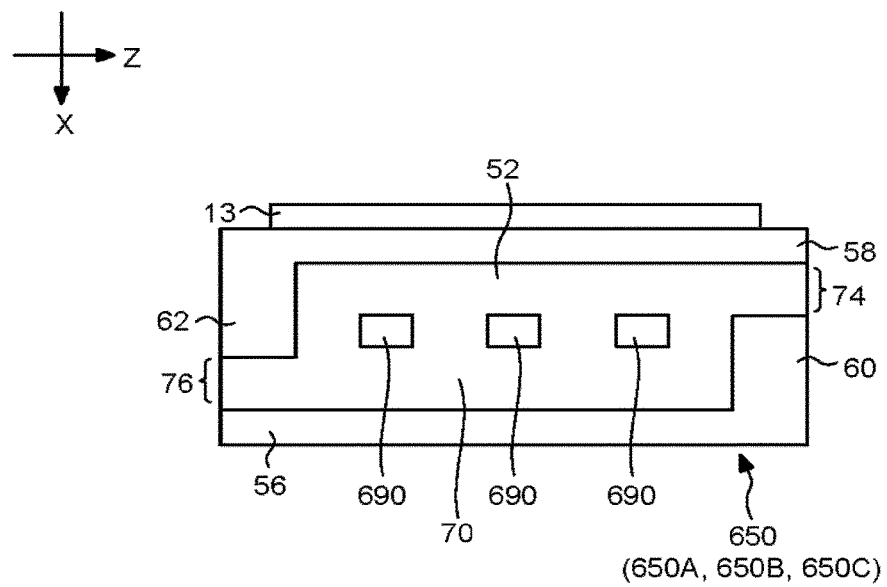
FIG. 23 is a schematic side view of an example of a supporting member according to a sixth modification.
Figure 24:
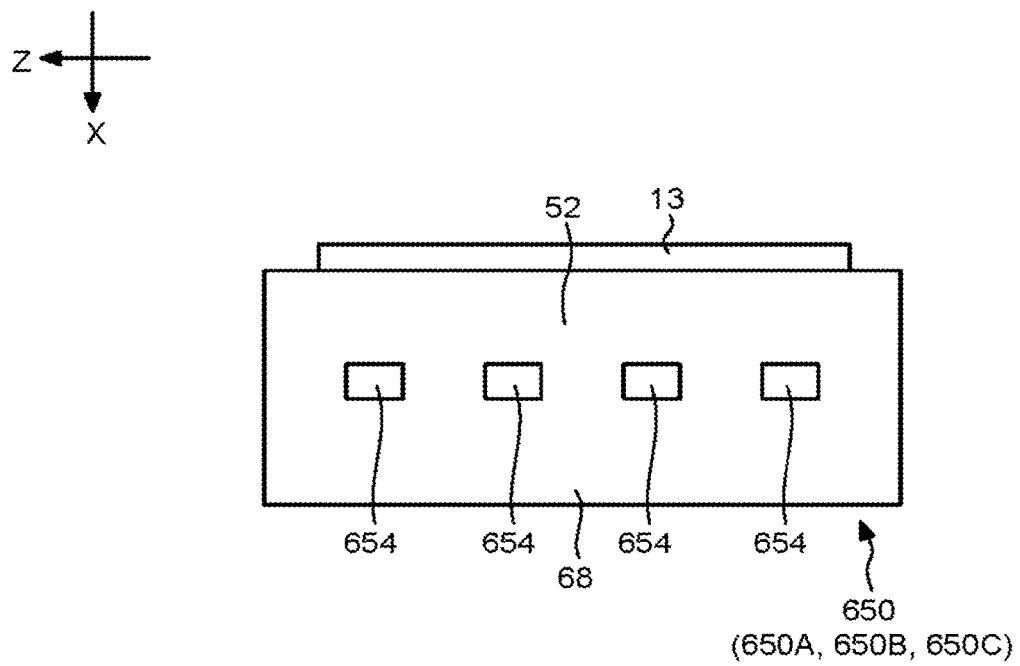
FIG. 24 is a schematic side view of the supporting member according to the sixth modification.
Figure 25:
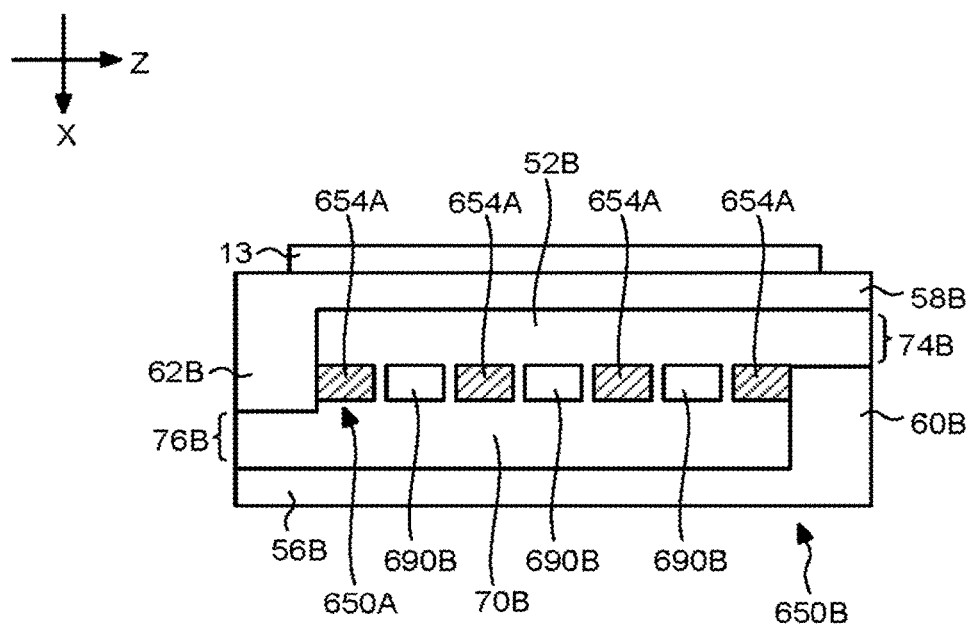
FIG. 25 is an exemplary schematic diagram for explaining the process of attaching the supporting member according to the sixth modification.

FIG. 23 is a schematic side view of an example of a supporting member according to a sixth modification. Herein, FIG. 23 is a side view of the supporting member from the side face 70. FIG. 24 is a schematic side view of an example of the supporting member according to the sixth modification. Herein, FIG. 24 is a side view of the supporting member from the side face 68. FIG. 25 is an exemplary schematic diagram for explaining the supporting member attaching process according to the sixth modification.

As illustrated in FIG. 23, a plurality of (for example, three) protrusions 690 is provided on the side face 70 of a supporting member 650. The protrusions 690 protrude from the side face 70. The protrusions 690 are disposed about the center of the side face 70 in the radial direction. However, the positions of the protrusions 690 should not be limited to be about the center of the side face 70 in the radial direction, and can be suitably changed according to the positions of first protrusions 654. Moreover, the protrusions 690 are aligned in the axis direction at substantially constant intervals between the first restrictor 60 and the second restrictor 62. However, the protrusions 690 do not need to be aligned in the axis direction at constant intervals, and the alignment can be suitably changed according to the positions of the first protrusions 654.

As illustrated in FIG. 24, the supporting member 650 has a plurality of (for example, four) first protrusions 654 on the side face 68. The first protrusions 654 protrude from the side face 68. Moreover, the first protrusions 654 are aligned about the center of the side face 68 in the radial direction. However, the positions of the first protrusions 654 should not be limited to about the center of the side face 68 in the radial direction, and can be suitably changed according to the positions of the protrusions 690. The first protrusions 654 are aligned in the axis direction at substantially constant intervals. More specifically, the first protrusions 654 are aligned with the gaps between the first restrictor 60, the protrusions 690, and the second restrictors 62. Thus, the alignment of the first protrusions 654 does not need to be at constant intervals in the axis direction, and can be suitably changed according to the positions of the protrusions 690.

Thus, for attaching a supporting member 650A in-between a supporting member 650B and a neighboring supporting member 650C on the opposite side, first protrusions 654A can be inserted into the gaps between the first restrictor 60B, protrusions 690B, and the second restrictor 62B.

Seventh Modification

Figure 26:
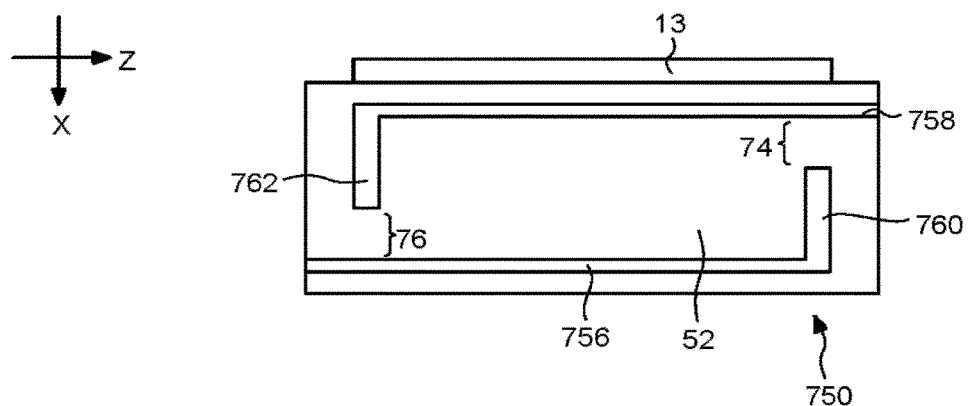
FIG. 26 is a schematic side view of an example of a supporting member according to a seventh modification.

FIG. 26 is a schematic side view of an example of a supporting member according to a seventh modification. As illustrated in FIG. 26, second protrusions 756 and 758, a first restrictor 760, and a second restrictor 762 can be configured to have narrower widths than the widths of the corresponding elements according to the first embodiment illustrated in FIG. 2. In other words, the second protrusions 756 and 758, the first restrictor 760, and the second restrictor 762 can be provided at positions away from the sides of the side face 70.

Eighth Modification

Figure 27:
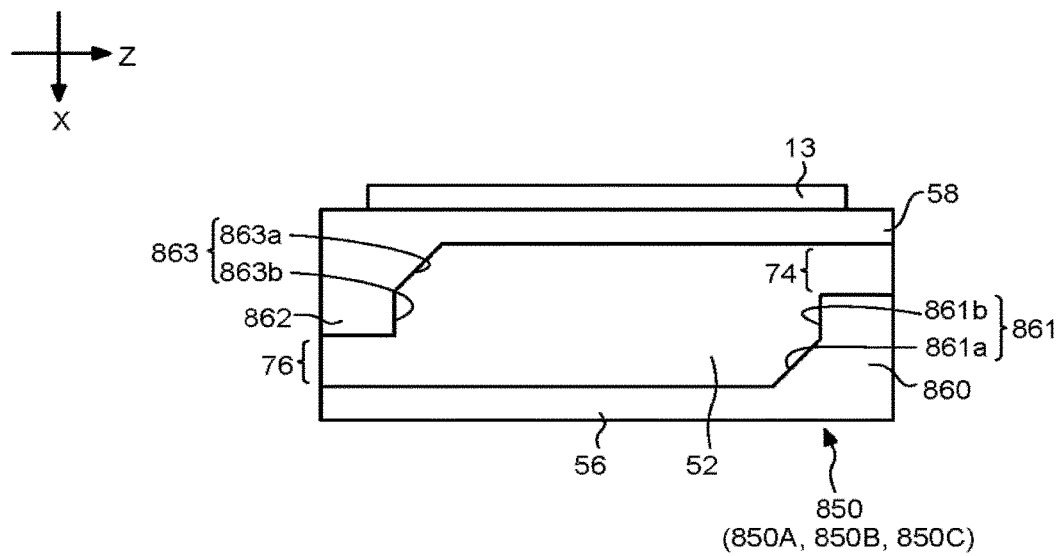
FIG. 27 is a schematic side view of an example of a supporting member according to an eighth modification.
Figure 28:
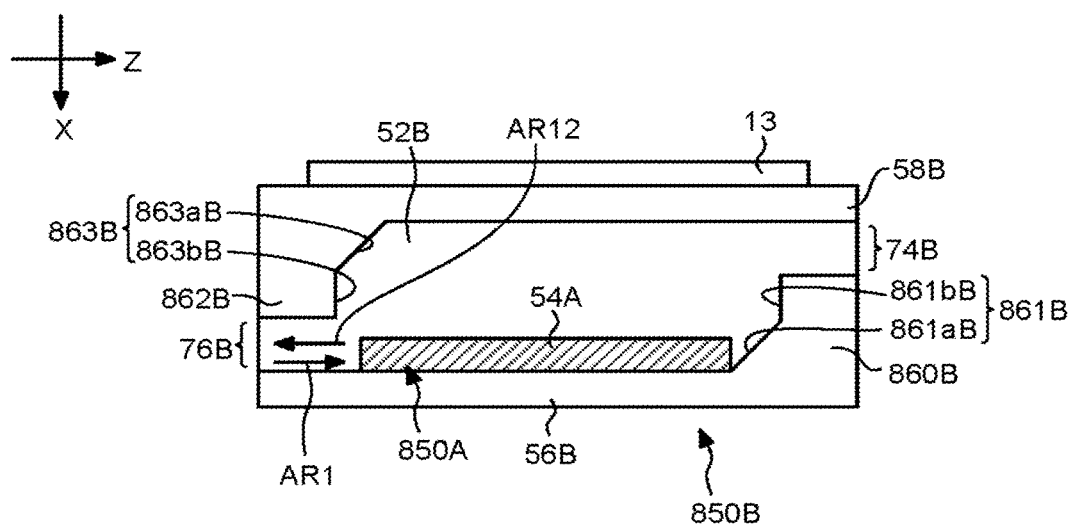
FIGS. 28 and 29 are exemplary schematic diagrams for explaining the process of attaching the supporting member according to the eighth modification.
Figure 29:
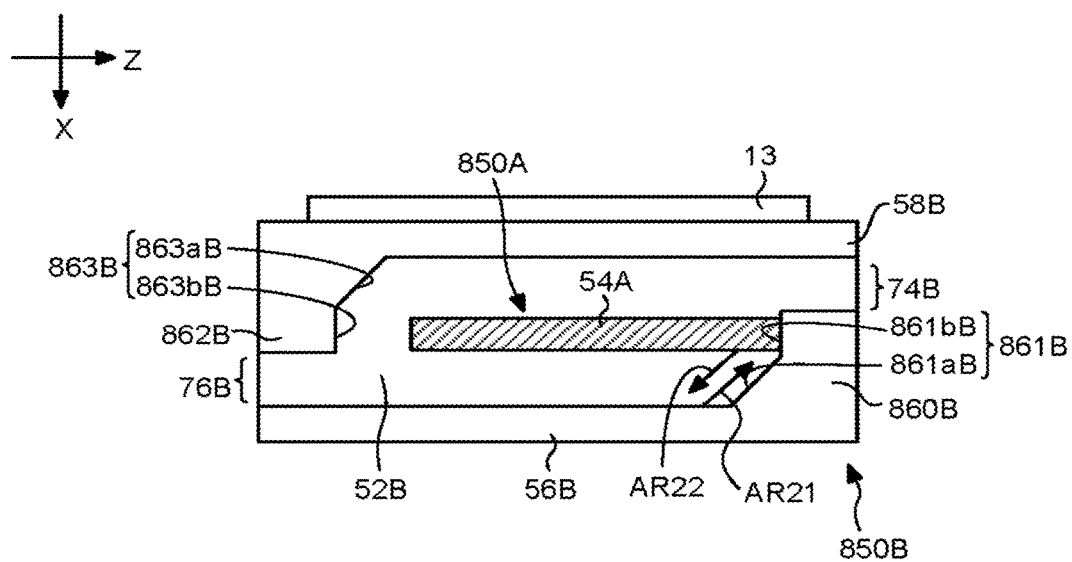

FIG. 27 is a schematic side view of an example of a supporting member according to an eighth modification. FIGS. 28 and 29 are exemplary schematic diagrams for explaining the supporting member attaching process according to the eighth modification. As illustrated in FIG. 27, a supporting member 850 includes a first restrictor 860 with a face 861 having an inclined face 861a and a restricting face 861b. The inclined face 861a is provided closer to the second protrusion 56 than the restricting face 861b. Moreover, the inclined face 861a is inclined with respect to the second protrusion 56. The restricting face 861b is in parallel to the radial direction. A face 863 of a second restrictor 862 includes an inclined face 863a and a restricting face 863b. The inclined face 863a is provided closer to the second protrusion 58 than the restricting face 863b. Moreover, the inclined face 863a is inclined with respect to the second protrusion 58. The restricting face 863b is in parallel to the radial direction.

In the process of attaching a supporting member 850A according to the eighth modification, the first protrusion 54A of the supporting member 850A is guided by the second protrusion 56B of a supporting member 850B to move in the positive Z direction as indicated by the arrow AR1 in FIG. 28. The first protrusion 54A makes contact with and is guided by an inclined face 861aB of the supporting member 850B. Hence, the supporting member 850A is moved in an obliquely upward as indicated by an arrow AR21 in FIG. 29. Herein, the obliquely upward refers to the direction toward the center of the radial direction and intersecting with the radial direction and the axis direction. The supporting member 850A stops moving when the first protrusion 54A contacts the inclined face 861aB. This stop position is the assembly position of the supporting member 850A. Accordingly, the restricting face 861b serves as a positioning face. Alternatively, a restricting face 863bB can serve as the positioning face. Then, the supporting member 850A is fixed at the stop position, completing the attaching process.

In the process of detaching the supporting member 850A according to the eighth modification, since the first protrusion 54A is guided by the inclined face 861aB, the supporting member 850A is moved obliquely downward (radially outside) as indicated by an arrow AR22 in FIG. 29. The supporting member 850A is moved until the first protrusion 54A contacts the second protrusion 56B. Then, the supporting member 850A is moved in the negative Z direction as indicated by the arrow AR12 and detached from supporting members 850B and 850C.

In the supporting member 850 according to the eighth modification, the first restrictor 860 includes the inclined face 861a relative to the axis direction. The inclined face 861a can function to reduce the impact from the contact between the axially moving first protrusion 54A of the supporting member 850A and a first restrictor 860B of the neighboring supporting member 850B.

Ninth Modification

Figure 30:
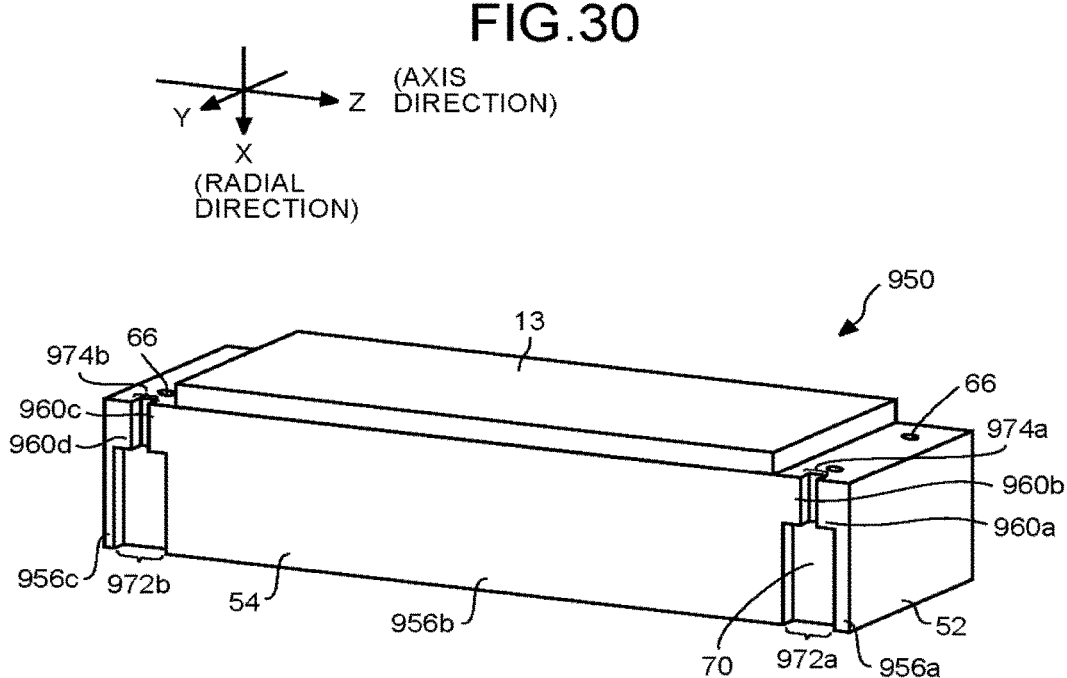
FIGS. 30 and 31 are exemplary schematic views of a supporting member according to a ninth modification.
Figure 31:
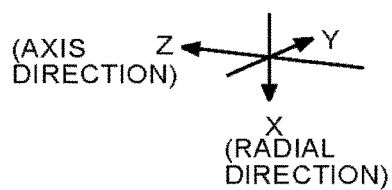
Figure 31:
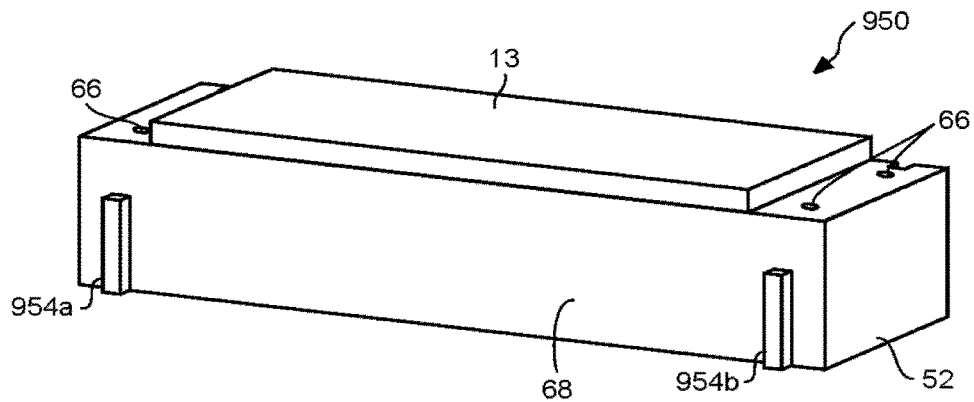

FIGS. 30 and 31 are exemplary schematic perspective views of a supporting member according to a ninth modification. FIG. 31 is a perspective view of a supporting member 950 from the positive Y side. FIG. 3 is a perspective view of the supporting member 950 from the negative Y side.

As illustrated in FIGS. 30 and 31, the supporting member 950 includes a body 52, two first protrusions 954a and 954b, three second protrusions 956a, 956b, and 956c, and four first restrictors 960a, 960b, 960c, and 960d. Herein, the two first protrusions 954a and 954b, the three second protrusions 956a, 956b, and 956c, and the four first restrictors 960a, 960b, 960c, and 960d are integrally provided on the body 52.

The two first protrusions 954a and 954b are provided on one side face 68 of the supporting member 950 in the circumferential direction. The two first protrusions 954a and 954b have a cuboid shape and radially extend. The length of the first protrusions 954a and 954b is shorter than the radial length of the body 52. One ends of the first protrusions 954a and 954b extend to one end of the body 52 in the positive X direction. The other ends of the first protrusions 954a and 954b are spaced from the other end of the body 52 in the negative X direction. The first protrusion 954a is provided near one end of the body 52 in the positive Z direction. The first protrusion 954b is provided near the other end of the body 52 in the negative Z direction. The first protrusion 954a and 954b are arranged with a spacing.

The three second protrusions 956a, 956b, and 956c are provided on the other side face 70 of the supporting member 950 in the circumferential direction. The three second protrusions 956a, 956b, and 956c radially extend over the substantially entire length of the side face 70. The second protrusion 956a is provided at the positive Z end of the other side face of the supporting member 950. The second protrusion 956b is provided at the center of the other side face of the supporting member 950 in the axis direction (the Z direction). The second protrusion 956c is provided at the negative Z end of the other side face of the supporting member 950.

The second protrusions 956a and 956b are arranged with a gap 972a in the axis direction. The gap 972a radially extends. The width of the gap 972a is greater than the width of the first protrusion 954a in the axis direction. The second protrusions 956a and 956b are arranged with a gap 972b in the axis direction. The gap 972b radially extends. The width of the gap 972b is greater than the width of the first protrusion 954b in the axis direction. The three second protrusions 956a, 956b and 956c guide the two first protrusions 954a and 954b in the radial direction along the gaps 972a and 972b. Hence, the two first protrusions 954a and 954b can move in the axis direction in-between the three second protrusions 956a, 956b and 956c. The two first protrusions 954a and 954b of a neighboring supporting member 950 are inserted into the gaps 972a and 972b of the three second protrusions 956a, 956b, and 956c and the three second protrusions 956a, 956b, and 956c overlap the first protrusions 954a and 954b of the neighboring supporting member 950 in the axis direction.

The four first restrictors 960a, 960b, 960c, and 960d are provided at the negative X end of the other side face 70 of the supporting member 950. The four first restrictors 960a, 960b, 960c and 960d are provided in continuation with the second protrusions 956a, 956b, and 956c. The two first restrictors 960a and 960d extend inward from the second protrusions 956a and 956c in the axis direction. The two first restrictors 960b and 960c extend outward from the second protrusion 956b in the axis direction. As a result, the four first restrictors 960a, 960b, 960c, and 960d restrict the movement of the two first protrusions 954a and 954b in the negative X direction. The two first restrictors 960a and 960b are arranged with a gap 974a. The width of the gap 974a is greater than the width of the first protrusion 954a in the axis direction. The two first restrictors 960c and 960d are arranged with a gap 974b. The width of the gap 974b is greater than the width of the first protrusion 954b in the axis direction. The width of the gaps 974a and 974b is smaller than the width of the gaps 972a and 972b in the axis direction.

Tenth Modification

Figure 32:
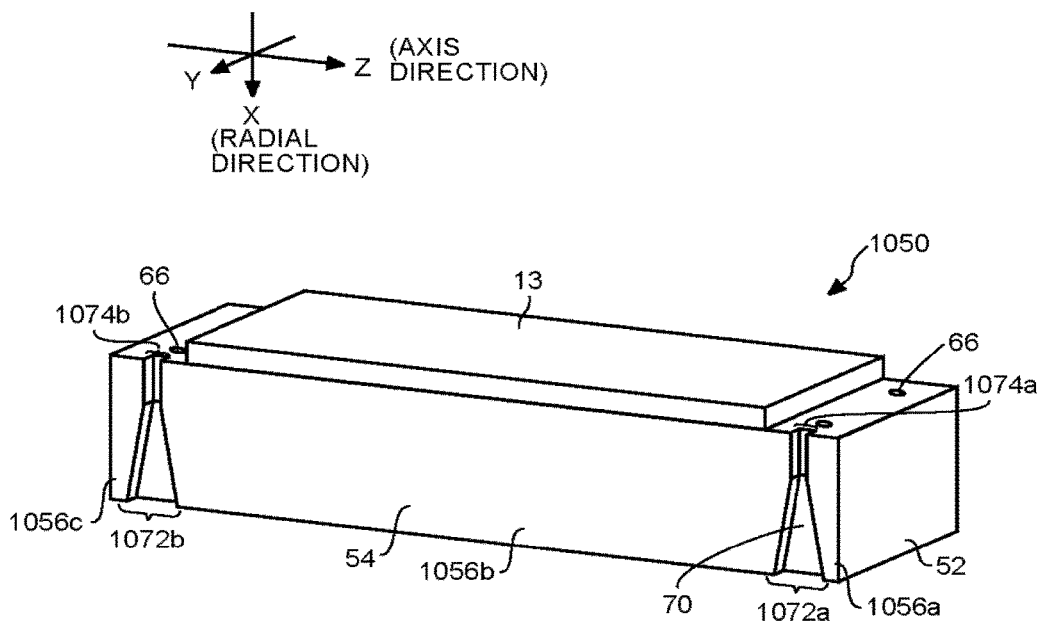
FIGS. 32 and 33 are exemplary schematic views of a supporting member according to a tenth modification.
Figure 33:
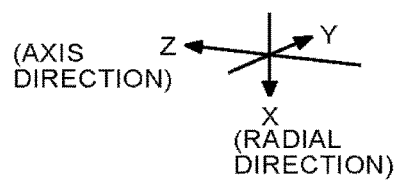
Figure 33:
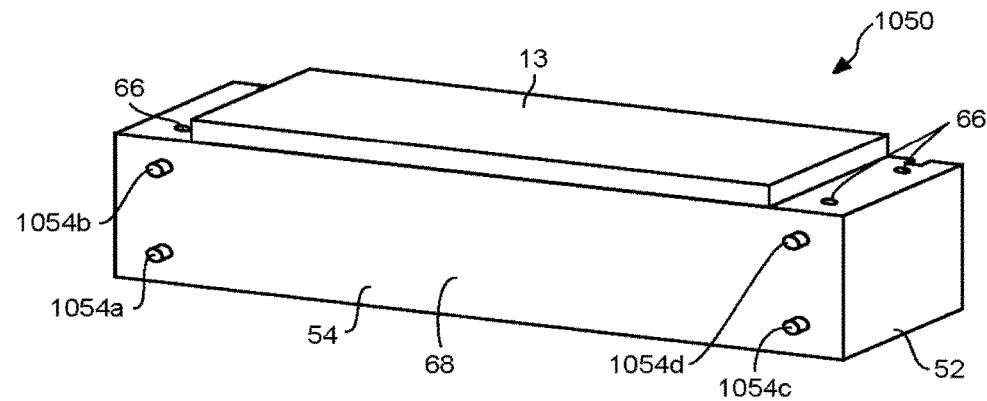

FIGS. 32 and 33 are exemplary schematic perspective views of a supporting member according to a tenth modification. FIG. 32 is a perspective view of a supporting member 1050 from the positive Y side. FIG. 33 is a perspective view of the supporting member 1050 from the negative Y side.

As illustrated in FIGS. 32 and 33, the supporting member 1050 includes a body 52, four first protrusions 1054a, 1054b, 1054c, and 1054d and three second protrusions 1056a, 1056b, and 1056c. Herein, the three second protrusions 1056a, 1056b, and 1056c are integrally provided on the body 52.

The four first protrusions 1054a, 1054b, 1054c, and 1054d are provided on one side face 68 of the supporting member 1050 in the circumferential direction. The four first protrusions 1054a, 1054b, 1054c, and 1054d have a cylindrical shape and extend in the circumferential direction.

For example, the first protrusions 1054a, 1054b, 1054c, and 1054d are inserted into holes of approximately the same shape formed in the one side face 68. The first protrusions 1054a, 1054b, 1054c, and 1054d may be integrally provided on the body 52. The two first protrusions 1054a and 1054b are disposed at the same position in the axis direction. The first protrusions 1054a and 1054b are disposed at different positions in the radial direction. The two first protrusions 1054c and 1054d are disposed the same positions in the axis direction. The first protrusions 1054c and 1054d are disposed at different positions in the radial direction. The two first protrusions 1054a and 1054b are disposed at the positions different from the two first protrusions 1054c and 1054d in the axis direction. The four first protrusions 1054a, 1054b, 1054c and 1054d are spaced from the radial ends of the body 52.

The three second protrusions 1056a, 1056b, and 1056c are provided on the other side face 70 of the supporting member 1050 in the circumferential direction. The three second protrusions 1056a, 1056b, and 1056c radially extend over the substantially entire length of the other side face 70 of the supporting member 1050. The second protrusion 1056a is provided at the positive Z end of the other side face 70 of the supporting member 1050. The second protrusion 1056b is provided at the center of the other side face 70 of the supporting member 1050 in the axis direction (Z direction). The second protrusion 1056c is provided at the negative Z end of the other side face 70 of the supporting member 1050.

Parts (for example, lower parts) of the two second protrusions 1056a and 1056b are arranged with a gap 1072a in the axis direction. The gap 1072a radially extends. The width of the gap 1072a is greater than the width of the first protrusions 1054a and 1054b in the axis direction. At least a part of the gap 1072a is tapered to be narrower in width in the negative X direction. Parts (for example, lower parts) of the two second protrusions 1056c and 1056b are arranged with a gap 1072b in the axis direction. The gap 1072b radially extends. The width of the gap 1072b is greater than the width of the first protrusions 1054c and 1054d in the axis direction. At least a part of the gap 1072b is tapered to be narrower in width in the negative X direction.

The three second protrusions 1056a, 1056b, and 1056c guide the four first protrusions 1054a, 1054b, 1054c and 1054d in the radial direction along the gaps 1072a and 1072b. Hence, the four first protrusions 1054a, 1054b, 1054c, and 1054d can move in the axis direction in-between the three second protrusions 1056a, 1056b and 1056c. Since the gaps 1072a and 1072b are tapered, the four first protrusions 1054a, 1054b, 1054c and 1054d can be easily inserted into the gaps 1072a and 1072b.

The other parts (for example, upper parts) of the two second protrusions 1056a and 1056b are arranged with a non-tapered gap 1074a. The width of the gap 1074a is greater than the width of the first protrusions 1054a and 1054b in the axis direction. The other parts (for example, upper parts) of the two second protrusions 1056b and 1056c are arranged with a non-tapered gap 1074b. The width of the gap 1074b is greater than the width of the first protrusions 1054c and 1054d in the axis direction. The width of the gaps 1074a and 1074b is approximately the same as the width of one ends (ex. upper ends) of the gaps 1072a and 1072b in the axis direction.

The above embodiment has described an example in which the first protrusion and the second protrusions are rectangular in shape. However, the shape thereof should not be limited to the rectangular shape. Moreover, the movement path of the first protrusion can be curved.

The second protrusions may overlap with the first protrusion of a neighboring one of the supporting members in a intersecting direction that intersects with the circumferential direction other than the radial direction and the axis direction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photographing device, comprising:
   a plurality of detectors that detects X-rays; and
   a plurality of supporting members cylindrically arranged adjacent to each other to support the detectors, wherein
   each of the supporting members includes
      a first protrusion on one side face in a circumferential direction of cylindrical arrangement of the supporting members, to protrude in the circumferential direction, and
      two second protrusions
         that protrude in the circumferential direction from the other side face,
         that are provided with a gap greater than a width of the first protrusion in an intersecting direction that intersects with the circumferential direction of the cylindrical arrangement, and
         that overlap with a first protrusion of a neighboring one of the supporting members in the intersecting direction.

2. The photographing device according to claim 1, wherein the intersecting direction represents a radial direction of the cylindrical arrangement.

3. The photographing device according to claim 2, wherein a first restrictor is provided on one end of the other side face in an axis direction of the cylindrical arrangement, and the first restrictor restricts movement of the first protrusion of the neighboring supporting member in at least either the axis direction or the radial direction.

4. The photographing device according to claim 3, wherein the first restrictor is provided in continuation with one of the second protrusions.

5. The photographing device according to claim 3, wherein the first restrictor is provided with a gap with the other second protrusions in the radial direction.

6. The photographing device according to claim 3, wherein a second restrictor is provided on other end of the other side face in the axis direction, and the second restrictor restricts movement of the first protrusion of the neighboring supporting member in at least either the axis direction or the radial direction.

7. The photographing device according to claim 6, wherein the second restrictor is provided in continuation with the other second protrusions.

8. The photographing device according to claim 6, wherein the second restrictor is provided with a gap with one of the second protrusions in the radial direction.

9. The photographing device according to claim 6, wherein the two second protrusions form a path through which the first protrusion of the neighboring supporting member moves.

10. The photographing device according to claim 9, wherein two first paths are formed by the first restrictor and other of the second protrusions and by the second restrictor and the one of the second protrusions, the two first paths are configured to guide the first protrusion of the neighboring supporting member in the axis direction.

11. The photographing device according to claim 10, wherein a second path is formed by the first restrictor and second restrictor, the second path is configured to guide the first protrusion of the neighboring supporting member in the radial direction.

12. The photographing device according to claim 11, wherein the second path is placed between the two first paths.

13. The photographing device according to claim 1, wherein the intersecting direction represents a direction along an axis of the cylindrical arrangement.

* * * * *